United States Patent
Gaab et al.

(10) Patent No.: US 9,636,668 B2
(45) Date of Patent: May 2, 2017

(54) PRODUCTION AND USE OF A ZEOLITIC MATERIAL IN A PROCESS FOR THE CONVERSION OF OXYGENATES TO OLEFINS

(71) Applicant: BASF SE, Ludwigshafen (DE)

(72) Inventors: Manuela Gaab, Heidelberg (DE); Ulrich Müller, Neustadt (DE); Milan Kostur, Mutterstadt (DE); Kirsten Spannhoff, Ludwigshafen (DE); Kerem Bay, Ludwigshafen (DE); Andrei-Nicolae Parvulescu, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 586 days.

(21) Appl. No.: 14/076,651

(22) Filed: Nov. 11, 2013

(65) Prior Publication Data
US 2014/0135556 A1    May 15, 2014

Related U.S. Application Data

(60) Provisional application No. 61/725,510, filed on Nov. 13, 2012.

(51) Int. Cl.
| | | |
|---|---|---|
| B01J 29/40 | (2006.01) | |
| B01J 37/02 | (2006.01) | |
| B01J 29/70 | (2006.01) | |
| B01J 23/02 | (2006.01) | |
| B01J 37/00 | (2006.01) | |
| C07C 1/20 | (2006.01) | |

(52) U.S. Cl.
CPC .......... *B01J 29/7038* (2013.01); *B01J 23/02* (2013.01); *B01J 29/40* (2013.01); *B01J 37/0009* (2013.01); *B01J 37/0201* (2013.01); *C07C 1/20* (2013.01); *B01J 29/7034* (2013.01); *C07C 2523/02* (2013.01); *C07C 2529/035* (2013.01); *C07C 2529/40* (2013.01); *C07C 2529/70* (2013.01); *Y02P 20/52* (2015.11)

(58) Field of Classification Search
CPC ........ B01J 29/40; B01J 29/70; B01J 29/7038; B01J 37/0201; C07C 2529/40
See application file for complete search history.

(56) References Cited

U.S. PATENT DOCUMENTS

| | | | | |
|---|---|---|---|---|
| 4,049,573 A | | 9/1977 | Kaeding | |
| 5,399,336 A | * | 3/1995 | Guth | ........................ B01J 29/04 423/326 |
| 5,409,682 A | * | 4/1995 | Mueller | .............. C01B 35/1009 423/277 |
| 8,981,173 B2 | * | 3/2015 | Nesterenko | .............. B01J 29/40 585/638 |
| 2007/0032379 A1 | * | 2/2007 | Ito | ........................... B01J 29/40 502/213 |
| 2007/0135637 A1 | | 6/2007 | Bosch et al. | |
| 2011/0144335 A1 | | 6/2011 | Bosch et al. | |

FOREIGN PATENT DOCUMENTS

| | | |
|---|---|---|
| CN | 1901993 | 1/2007 |
| CN | 101145823 | 3/2008 |
| DE | 238733 | 9/1986 |
| DE | 4131448 | 3/1993 |
| DE | 10356184 | 7/2005 |
| EP | 0 178 687 A2 | 4/1986 |
| EP | 2460784 | 6/2012 |
| WO | WO 2011/089263 A1 | 7/2011 |

OTHER PUBLICATIONS

Zeolyst, ZSM-5, http://www.zeolyst.com/our-products/standard-zeolite-powders/zsm-5.aspx, downloaded Jun. 6, 2016.*
PCT International Search Report and Written Opinion in PCT/IB2013/060057, mailed Mar. 6, 2014, 13 pages.
Ciambelli, P. et al., "Acid-Base Catalysis in the Conversion of Methanol to Olefins Over Mg-Modified ZSM5 Zeolite", T. Inui, *Successful Design of Catalysts* 1988 , 239-246.
Goryainova, T.I. et al., "Study of Magnesium-Containing Zeolite Catalysts for the Synthesis of Lower Olefins from Dimethyl Ether", *Petroleum Chemistry*, vol. 51 2011 , 169-173.
McIntosh, Rosemary J. et al., "The Properties of Magnesium and Zinc Oxide Treated ZSM-5 Catalysts for Conversion of Methanol Into Olefin-Rich Products", *Applied Catalysis*, 6 1983 , 307-314.
Okado, Hideo et al., "Deactivation Resistance of ZSM-5-Type Zeolites Containing Alkaline Earth Metals used for Methanol Conversion", *Applied Catalysis*, 41 1988 , 121-135.
Ahedi, Ranjeet K. et al., "Synthesis of FER titanosilicates from a non-aqueous alkali-free seeded system", *Journal of Materials Chemistry*, vol. 8 1998 , 1685-1686.
De Baerdemaeker, Trees et al., "Alkali-free synthesis of Al-MTW using 4-cyclohexyl-1,1-dimethylpiperazinium hydroxide as structure directing agent", *Microporous and Mesoporous Materials*, vol. 143 2011 , 477-481.
Dodwell, Glenn W. et al., "Crystallization of EU-1 and EU-2 in Alkali and Alkali-Free Systems", *Zeolites*, vol. 5 1985 , 153-157.
Liu, Na et al., "A New Synthesis Route for MWW Analogues Using Octyltrimethylammonium Cations as Structure-directing Agents under Alkali-free Conditions", *Chemistry Letters* vol. 36, No. 7 Jun. 23, 2007 , 916-917.

(Continued)

*Primary Examiner* — David M Brunsman
(74) *Attorney, Agent, or Firm* — Oblon, McClelland, Maier & Neustadt, L.L.P.

(57) ABSTRACT

Described is a process for the production of a zeolitic material having an MFI, MEL, and/or MWW-type framework structure comprising $YO_2$ and $X_2O_3$. The process comprises (1) preparing a mixture comprising one or more sources for $YO_2$, one or more sources for $X_2O_3$, and one or more solvents; (2) crystallizing the mixture obtained in step (1) to obtain a zeolitic material having an MFI, MEL and/or MWW-type framework structure; and (3) impregnating the zeolitic material obtained in step (2) with one or more elements selected from the group of alkaline earth metals. Y is a tetravalent element, and X is a trivalent element. The mixture crystallized in step (2) contains 3 wt.-% or less of one or more elements M based on 100 wt.-% of $YO_2$, wherein M stands for sodium.

48 Claims, 11 Drawing Sheets

(56) References Cited

OTHER PUBLICATIONS

Reding, Gilles et al., "Comparing synthesis routes to nano-crystalline zeolite ZSM-5", *Microporous and Mesoporous Materials*, vol. 57 2003, 83-92.
Rivas-Cardona, Alejandra et al., "A systematic investigation of silicalite-1 precursor mixtures with varying degrees of dilution", *Microporous and Mesoporous Materials*, vol. 155 2012, 56-64.
Shibata, Masashi et al., "Synthesis of alkali-free MFI borosilicates from methylamine-SiCl4 media", *Applied Catalysis A: General 162* 1997, 93-102.
Takeguchi, Tatsuya et al., "Synthesis and Characterization of Alkali-free, Ga-Substituted MCM-41 and Its Performance for n-Hexane Conversion", *Journal of Catalysis*, vol. 175 1998, 1-6.
Van Grieken, R. et al., "Anomalous crystallization mechanism in the synthesis of nanocrystalline ZSM-5", *Microporous and Mesoporous Materials*, vol. 39 2000, 135-147.
Partial Supplementary Search Report issued Jul. 13, 2016 in European Patent Application No. 13855440.7.
Kanna Aoki, et al., "Gas permeation properties of ion-exchanged ZSM-5 zeolite membranes", Microporous and Mesoporous Materials, vol. 39, No. 3, XP004217701, 2000, pp. 485-492.
Extended European Search Report issued Nov. 8, 2016 in Patent Application No. 13855440.7.
Raymond Le Van Mao, et al., "Composite ZSM-5 zeolite/asbestos catalysts" Canadian Journal of Chemistry, vol. 63, XP55112794, 1985, pp. 3464-3470.
Ali A. Rownaghi, et al., "Yield of gasoline-range hydrocarbons as a function of uniform ZSM-5 crystal size" Catalysis Communications, vol. 14, XP28286827, 2011, pp. 37-41.

\* cited by examiner

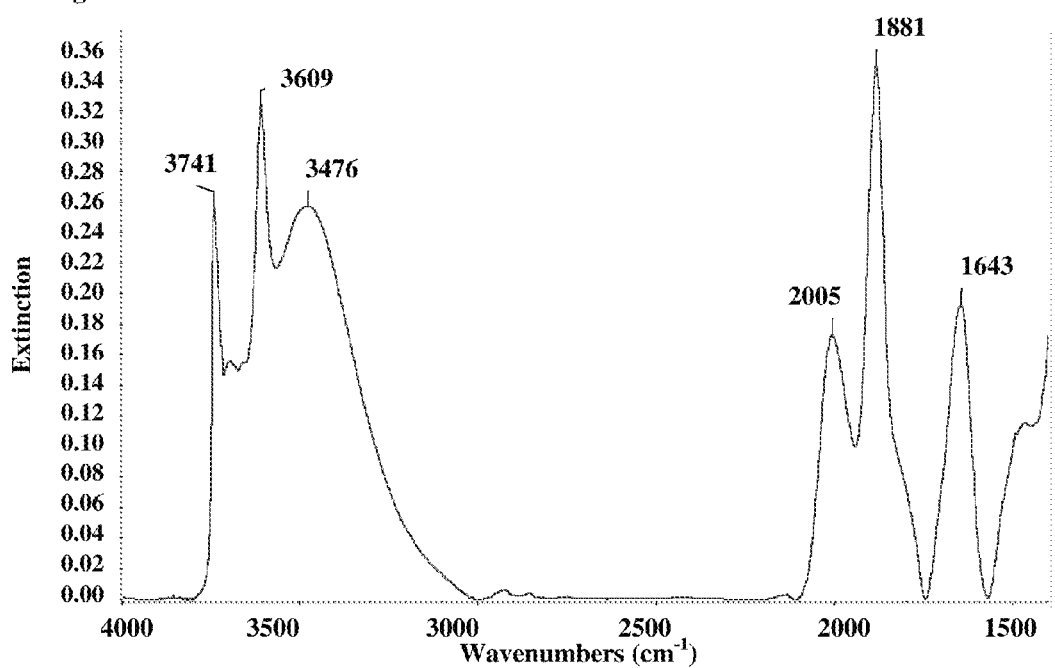

PRODUCTION AND USE OF A ZEOLITIC MATERIAL IN A PROCESS FOR THE CONVERSION OF OXYGENATES TO OLEFINS

CROSS-REFERENCE TO RELATED APPLICATIONS

This application claims the benefit of priority under 35 U.S.C. §119(e) to U.S. Provisional Application No. 61/725,510, filed Nov. 13, 2012, the entire content of which is incorporated herein by reference in its entirety.

TECHNICAL FIELD

The present invention relates to a process for the production of a zeolitic material having an MFI, MEL, and/or MWW-type framework structure. Furthermore, the present invention relates to a zeolitic material having an MFI, MEL, and/or MWW-type framework structure as such and to its use in a process for the conversion of oxygenates to olefins. Finally, the present invention further relates to the use of a zeolitic material having an MFI, MEL, and/or MWW-type framework structure according to the present invention.

BACKGROUND

In view of the decreasing amount of oil reserves which constitute the raw material for the production of short-chain hydrocarbons and derivatives thereof, alternative processes for the production of such base chemicals are of a growing importance. In such alternative processes for the production of short-chain hydrocarbons and derivatives thereof, often highly specific catalysts are used therein for converting other raw materials and/or chemicals to hydrocarbons and their derivatives such as in particular short-chain olefins. A particular challenge involved in such processes not only relies in the optimal choice of reaction parameters but, more importantly, in the use of particular catalysts allowing for the highly efficient and selective conversion to a desired hydrocarbon or derivative thereof such as in particular olefinic fractions. In this respect, processes in which methanol is employed as the starting material, are of particular importance, wherein their catalytic conversion usually leads to a mixture of hydrocarbons and derivatives thereof, in particular olefins, paraffins, and aromatics.

Thus, the particular challenge in such catalytic conversions resides in the optimization and the fine tuning of the catalysts employed as well as the process architecture and parameters such that as high a selectivity towards as few products as possible may be achieved. For this reason, such processes are often named after the products for which a particularly high selectivity may be achieved in the process. Accordingly, processes which have been developed in the past decades towards the conversion of oxygenates to olefins and in particular of methanol to olefins which have gained increasing importance in view of dwindling oil reserves are accordingly designated as methanol-to-olefin-processes (MTO-processes for methanol to olefins).

Among the catalytic materials which have been found for use in such conversions, zeolitic materials have proven of high efficiency, wherein in particular zeolitic materials of the pentasil-type and more specifically those having an MFI-and MEL-type framework structures including such zeolites displaying an MFI-MEL-intergrowth type framework structure are employed. As regards the specific application of zeolitic materials and in particular zeolitic materials of the pentasil-type in catalysis and more particularly in processes for the conversion of oxygenates to olefins such as the MTO-processes discussed in the foregoing, EP 2 460 784 A1 relates to a method for producing propylene from an oxygen-containing compound using a catalyst which can keep its stable activity for a prolonged period of time in the manufacturing process. DD 238 733 A1 relates to a synthetic procedure for the preparation of selective olefin catalysts. McIntosh et al. in Applied Catalysis 1983, vol. 6, pp. 307-314 concerns the properties of magnesium and zinc oxide treated ZSM-5 catalysts for the conversion of methanol into olefin-rich products. Likewise, Ciambelli et al. in "Acid-Base Catalysis in the Conversion of Methanol to Olefins over Mg-Modified ZSM-5 Zeolite", Successful Design of Catalysts, edited by T. Inui, Elsevier Science Publishers B.V., Amsterdam 1988 investigates the effect of magnesium in pure and bonded ZSM-5 catalysts, in particular on the acid-base properties and their effect on olefin selectivities in the MTO-process.

In the aim of further improving the properties of such catalysts, their further treatment with specific compounds has been investigated, wherein in particular the microporous system typical of these zeolitic materials may be loaded with different compounds. Thus, Okado et al. in Applied Catalysis 1988, vol. 41, pp. 121-135 concerns the deactivation resistance of ZSM-5-type zeolites containing alkaline earth metals and their use in the conversion of methanol. Similarly, Goryainova et al. in Petroleum Chemistry 2011, vol. 51, pp. 169-173 investigates on magnesium-containing zeolite catalysts for the synthesis of lower olefins from dimethyl ether. U.S. Pat. No. 4,049,573, on the other hand, concerns zeolite catalysts containing oxides of boron or magnesium.

On the other hand, as regards the synthesis of zeolitic materials in general, efforts have been invested into their optimization for economical and increasingly also for environmental reasons. In this respect, it has been found that crystallizing an aluminosilicate in the absence of an alkali source allows to omit the ion-exchange procedures normally required after crystallization to obtain the so called H-form thereof, wherein the alkali metals present in the resulting material as non-framework element are exchanged against protons. The ion exchanges necessitate additional steps in the manufacturing process considerably reducing the space-time-yield of the zeolite, generating high volumes of waste water, consuming energy and thus increasing overall production costs. Alkali-free synthetic methodologies are thus highly beneficial as it makes the synthesis process simpler with fewer steps, thus more economical and industrially viable. Such a manufacturing process also generates less waste during catalyst production.

Thus, Liu et al. in Chemistry Letters 2007, vol. 36, pp. 916 and 917, for example, concerns a synthetic procedure for the preparation of MWW-type metallosilicates under alkali-free conditions. The De Baerdemaeker et al. in Microporous and Mesoporous Materials 2011, vol. 143, pp. 477-481 concerns the synthesis of MTW-type zeolites which is performed in an alkali-free and fluoride-free synthetic procedure. In Takeguchi et al. in Journal of Catalysis 1998, vol. 175, pp. 1-6 the synthesis of alkali-free Ga-substituted MCM-41 catalysts is described. Ahedi et al. in Journal of Materials Chemistry 1998, vol. 8, pp. 1685-1686 concerns the synthesis of FER titanosilicates from a non-aqueous alkali-free seeded system. Dodwell et al. in Zeolites 1985, vol. 5, pp. 153-157 concerns the crystallization of EU-1 and EU-2 in alkali and alkali-free systems. Shibata et al. in Applied Catalysis A: General 1997, vol. 162, pp. 93-102, on the other hand, describes routes for the synthesis of alkali-free MFI borosilicates.

Furthermore it is now known that the formation, in particular the diameter, of the zeolite crystals obtained via alkali-free processes can be tuned by adjusting the temperature, stirring rate, concentration of the synthesis mixture and the duration of the crystallization. This may be of importance to adjust the diffusion properties of the zeolite for specific catalytic applications and to allow for optimal shaping and properties of the resulting shaped bodies. In particular, appropriate shaped bodies often need to be prepared prior to the introduction of the catalyst into a reactor to carry out the catalytic transformation.

In this respect, DE 103 56 184 A1 relates to a zeolitic material of the pentasil type having a molar ratio of Si to Al of from 250 to 1500, wherein furthermore at least 90% of the primary particles of the zeolitic material are spherical, wherein 95% by weight thereof have a diameter of less than or equal to 1 μm. Furthermore, said document discloses a specific treatment of ZSM-5 powder with demineralized water under autogeneous pressure, wherein it is taught that both the activity and the selectivity would be improved by the water treatment of the ZSM-5 powder under hydrothermal conditions when employed in a process for the preparation of tetraethylenediamine from piperazine and ethylenediamine. DE 41 31 448 A1 on the other hand concerns essentially alkali-free borous silicate crystals having a zeolite structure and a size from 2 to 150 μm.

Reding et al. in Microporous and Mesoporous Materials 2003, vol. 57, pp. 83-92 investigates on synthetic procedures for obtaining nano-crystalline zeolite ZSM-5. Likewise, Van Grieken in Microporous and Mesoporous Materials 2000, vol. 39, pp. 135-147 investigates the crystallization mechanism in the synthesis of nanocrystalline ZSM-5. Rivas-Cardona in Microporous and Mesoporous Materials 2012, vol. 155, pp. 56-64, on the other hand, investigates silicalite-1 precursor mixtures having varying degrees of dilution.

Despite the considerable efforts related by the prior art relative to the synthesis of novel zeolitic materials on the one hand by using new and improved synthetic procedures, and their various applications such as in particular in the field of catalysis on the other hand, there remains an ongoing need to provide new zeolitic materials displaying yet further improved properties in particular with respect to the large and constantly increasing number of applications in which they may be employed and in particular in the very important field of catalytic processes.

SUMMARY

A first aspect of the present invention is directed to a process for the production of a zeolitic material having an MFI, MEL, and/or MWW-type framework structure comprising $YO_2$ and $X_2O_3$. In a first embodiment, the process comprises (1) preparing a mixture comprising one or more sources for $YO_2$, one or more sources for $X_2O_3$, and one or more solvents; (2) crystallizing the mixture obtained in step (1) to obtain a zeolitic material having an MFI, MEL and/or MWW-type framework structure; and (3) impregnating the zeolitic material obtained in step (2) with one or more elements selected from the group of alkaline earth metals; wherein Y is a tetravalent element, and X is a trivalent element, and wherein the mixture crystallized in step (2) contains 3 wt.-% or less of one or more elements M based on 100 wt-% of $YO_2$, wherein M stands for sodium.

In a second embodiment, the process of the first embodiment is modified, wherein the mixture crystallized in step (2) contains 1 wt.-% or less of one or more elements M based on 100 wt-% of $YO_2$.

In a third embodiment, the process of the first and second embodiments is modified, wherein M comprises sodium, potassium, or mixtures thereof.

In a fourth embodiment, the process of the first through third embodiments is modified, wherein in step (3) the zeolitic material is impregnated with one or more elements selected from the group consisting of Mg, Ca, Ba, and Sr, and mixtures of two or more thereof.

In a fifth embodiment, the process of the first through fourth embodiments is modified, wherein the $YO_2:X_2O_3$ molar ratio of the mixture prepared in step (1) ranges from 10 to 1,500.

In a sixth embodiment, the process of the first through fifth embodiments is modified, wherein Y is selected from the group consisting of Si, Sn, Ti, Zr, Ge, and mixtures of two or more thereof.

In a seventh embodiment, the process of the first through sixth embodiments is modified, wherein X is selected from the group consisting of Al, B, In, Ga, and mixtures of two or more thereof.

In an eighth embodiment, the process of the first through seventh embodiments is modified, wherein the one or more solvents comprise one or more polar solvents.

In a ninth embodiment, the process of the first through eighth embodiments is modified, wherein the mixture in step (1) further comprises one or more organotemplates.

In a tenth embodiment, the process of the ninth embodiment is modified, wherein the one or more organotemplates comprises one or more tetraalkylammonium compounds selected from the group consisting of tetraethylammonium compounds, triethylpropylammonium compounds, diethyldipropylammonium compounds, ethyltripropylammonium compounds, tetrapropylammonium compounds, and mixtures of two or more thereof.

In an eleventh embodiment, the process of the ninth and tenth embodiments is modified, wherein the one or more organotemplates comprises one or more alkenyltrialkylammonium compounds selected from the group consisting of N—$(C_2-C_5)$alkenyl-tri-$(C_1-C_5)$alkylammonium compounds.

In a twelfth embodiment, the process of the ninth through eleventh embodiments is modified, wherein the molar ratio of the total amount of the one or more organotemplates of the mixture obtained in step (1) to $YO_2$ ranges from 1:(0.1-30).

In a thirteenth embodiment, the process of the first through twelfth embodiments is modified, wherein the mixture according to step (1) further comprises one or more sources for $OH^-$.

In a fourteenth embodiment, the process of the thirteenth embodiment is modified, wherein the $OH^-:YO_2$ molar ratio of the mixture obtained in step (1) ranges from 0.01 to 5.

In a fifteenth embodiment, the process of the first through fourteenth embodiments is modified, wherein the crystallization in step (2) involves heating of the mixture.

In a sixteenth embodiment, the process of the first through fifteenth embodiments is modified, wherein the crystallization in step (2) is conducted under solvothermal conditions.

In a seventeenth embodiment, the process of the first through sixteenth embodiments is modified, wherein the crystallization in step (2) involves heating of the mixture for at least 3 h.

In an eighteenth embodiment, the process of the first through seventeenth embodiments is modified, wherein after step (2) and prior to step (3) the process further comprises (2a) adjusting the pH of the product mixture obtained in (2) to a pH in the range of 5 to 9; and/or (2b) isolating the zeolitic material from the product mixture obtained in (2); and/or (2c) washing the zeolitic material; and/or (2d) drying and/or calcining the zeolitic material; and/or (2e) subjecting the zeolitic material to a hydrothermal treatment.

In a nineteenth embodiment, the process of the eighteenth embodiment is modified, wherein the calcination in step (2d) is conducted at a temperature in the range of 300 to 850° C.

In a twentieth embodiment, the process of the eighteenth and nineteenth embodiments is modified, wherein the hydrothermal treatment in step (2e) is conducted under autogenous pressure.

In a twenty-first embodiment, the process of the eighteenth through twentieth embodiments is modified, wherein the hydrothermal treatment in step (2e) is conducted using an aqueous solvent system, wherein specifically the aqueous solvent system consists of water, specifically of distilled water.

In a twenty-second embodiment, the process of the eighteenth through twenty-first embodiments is modified, wherein the hydrothermal treatment in step (2e) is conducted under heating, and specifically at a temperature ranging from 80 to 250° C., more specifically from 100 to 220° C., more specifically from 120 to 200° C., more specifically from 140 to 190° C., more specifically from 160 to 185° C., and more specifically from 170 to 180° C.

In a twenty-third embodiment, the process of the eighteenth through twenty-second embodiments is modified, wherein the hydrothermal treatment in step (2e) is conducted for a duration ranging from 2 to 72 h, specifically from 4 to 48 h, more specifically from 8 to 36 h, more specifically from 12 to 30 h, and more specifically from 18 to 24 h.

In a twenty-fourth embodiment, the process of the eighteenth through twenty-third embodiments is modified, wherein the hydrothermally treated zeolitic material obtained in step (2e) displays a water uptake of 10.0 wt.-% or less.

In a twenty-fifth embodiment, the process of the eighteenth through twenty-fourth embodiments is modified, wherein in step (3) the zeolitic material is impregnated with from 0.1 to 15 wt.-% of the one or more elements selected from the group of alkaline earth metals based on the total weight of the zeolitic material.

A second aspect of the present invention relates to a zeolitic material. In a twenty-sixth embodiment, the zeolitic material having an MFI, MEL, and/or MWW-type framework structure comprises $YO_2$ and $X_2O_3$, wherein Y is a tetravalent element, and X is a trivalent element, wherein the zeolitic material contains 3 wt.-% or less of one or more elements M based on 100 wt-% of $YO_2$, wherein M stands for sodium, wherein the zeolitic material further comprises one or more elements selected from the group of alkaline earth metals, and wherein 95% by weight or more of the primary particles have a diameter of less than or equal to 1 μm.

In a twenty-seventh embodiment, the zeolitic material of the twenty-sixth embodiment is modified, wherein the zeolitic material is obtainable and/or obtained by a process according to any one the first through twenty-fifth embodiments.

In a twenty-eighth embodiment, the zeolitic material of the twenty-sixth and twenty-seventh embodiments is modified, wherein 90% or more of the primary particles are spherical.

In a twenty-ninth embodiment, the zeolitic material of the twenty-sixth through the twenty-eighth embodiments is modified, wherein 95% by weight or more of the primary particles have a diameter of from 5 to 800 nm.

In a thirtieth embodiment, the zeolite material of the twenty-sixth through twenty-ninth embodiments is modified, wherein the zeolitic material contains 1 wt.-% or less of one or more elements M based on 100 wt-% of $YO_2$.

In a thirty-first embodiment, the zeolitic material of the twenty-sixth through thirtieth embodiments is modified, wherein M comprises sodium, potassium, and mixtures thereof.

In a thirty-second embodiment, the zeolitic material of the twenty-sixth through thirty-first embodiments is modified, wherein the one or more elements selected from the group of alkaline earth metals further comprised in the zeolitic material are contained in the zeolitic material in an amount ranging from 0.1 to 15 wt.-% based on the total weight of the zeolitic material.

In a thirty-third embodiment, the zeolitic material of the twenty-sixth through thirty-second embodiments is modified, wherein the one or more elements selected from the group of alkaline earth metals which are further comprised in the zeolitic material are selected from the group consisting of Mg, Ca, Ba, and Sr, and mixtures of two or more thereof.

In a thirty-fourth embodiment, the zeolitic material the twenty-sixth through thirty-third embodiments is modified, wherein the zeolitic material displays a $YO_2:X_2O_3$ atomic ratio of from 10 to 1,500.

In a thirty-fifth embodiment, the zeolitic material of the twenty-sixth through thirty-fourth embodiment is modified, wherein Y is selected from the group consisting of Si, Sn, Ti, Zr, Ge, and mixtures of two or more thereof.

In a thirty-sixth embodiment, the zeolitic material of the twenty-sixth through thirty-fifth embodiments is modified, wherein X is selected from the group consisting of Al, B, In, Ga, and mixtures of two or more thereof.

In a thirty-seventh embodiment, the zeolitic material of the twenty-sixth through thirty-sixth embodiments is modified, wherein the zeolitic material comprises ZSM-5.

In a thirty-eighth embodiment, the zeolitic material of the twenty-sixth through thirty-seventh embodiments is modified, wherein the BET surface area of the zeolitic material determined according to DIN 66131 ranges from 200 to 900 $m^2/g$.

In a thirty-ninth embodiment, the zeolitic material of the twenty-sixth through thirty-eighth embodiments is modified, wherein the zeolitic material displays a water uptake of 10.0 wt.-% or less.

A third aspect of the present invention is directed to a process for the conversion of oxygenates to olefins. In a fortieth embodiment, the process comprises (I) providing a gas stream comprising one or more oxygenates; (II) contacting the gas stream with a catalyst comprising a zeolitic material according to the twenty-sixth through thirty-ninth embodiments.

In a forty-first embodiment, the process of the fortieth embodiment is modified, wherein the gas stream provided in step (I) contains one or more oxygenates selected from the group consisting of aliphatic alcohols, ethers, carbonyl compounds, and mixtures of two or more thereof.

In a forty-second embodiment, the process of the fortieth and forty-first embodiment is modified, wherein the gas stream provided in step (I) contains from 30 to 100 vol.-% of oxygenates based on the total volume of the gas stream.

In a forty-third embodiment, the process of the fortieth through forty-second embodiments is modified, wherein the gas stream provided in step (i) contains 60 vol.-% or less of water based on the total volume of the gas stream.

In a forty-fourth embodiment, the process of the fortieth through forty-third embodiments is modified, wherein contacting of the gas stream with the catalyst in step (II) is performed at a temperature in the range of 200 to 700° C.

In a forty-fifth embodiment, the process of the fortieth through forty-fourth embodiments is modified, wherein contacting of the gas stream with the catalyst in step (II) is performed at a pressure in the range of 0.1 to 10 bar.

In a forty-sixth embodiment, the process of the fortieth through forty-fifth embodiments is modified, wherein the process is at least in part performed in a continuous mode.

In a forty-seventh embodiment, the process of the forty-sixth embodiment is modified, wherein the weight hourly space velocity (WHSV) of the gas stream in step (II) ranges from 0.5 to 50 h$^{-1}$.

A fourth aspect of the invention is directed to use of the zeolitic material of the twenty-sixth through thirty-ninth embodiments as a molecular sieve, catalyst, catalyst support, and/or as an adsorbent. In a forty-eighth embodiment, the method comprises adding the zeolitic material of the twenty-sixth through thirty-ninth embodiments as a molecular sieve, catalyst, catalyst support, and/or as an adsorbent to a reaction.

BRIEF DESCRIPTION OF THE DRAWINGS

FIGS. 1C, 2C, and 4C respectively show the IR spectra of the crystalline material obtained according to Reference Examples 1, 2, and 4. In the respective figures, the wavenumbers in cm$^{-1}$ is plotted along the abscissa and the absorbance in arbitrary units is plotted along the ordinate.

DETAILED DESCRIPTION

Figure 1A:
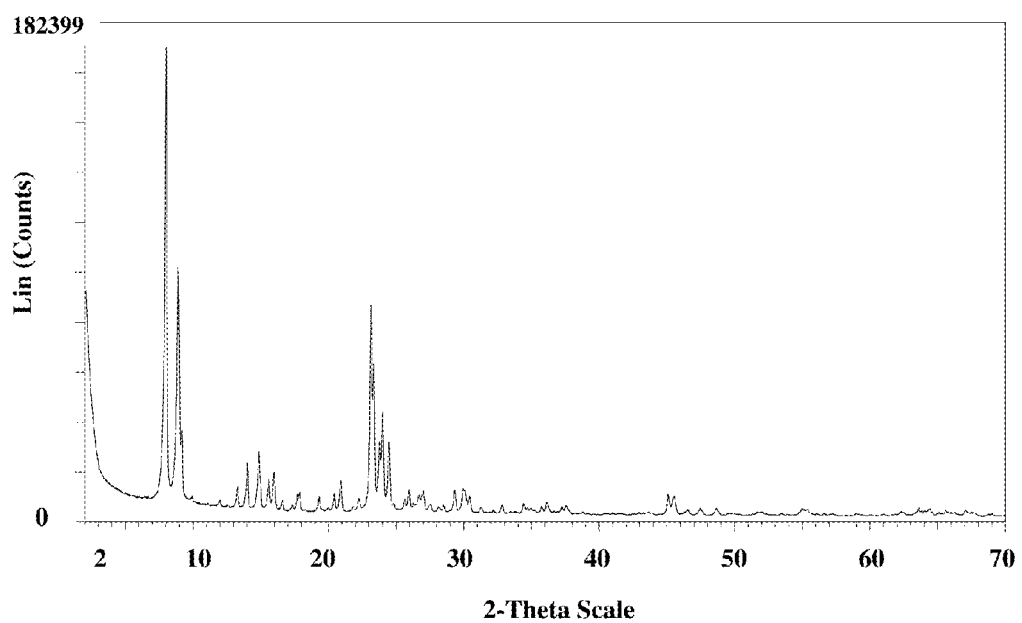
FIGS. 1A, 2A, 3A, and 4A show the X-ray diffraction patterns (measured using Cu K alpha-1 radiation) of the crystalline material obtained according to Reference Examples 1-4, respectively. In the respective figures, the angle 2 theta in ° is shown along the abscissa and the intensity in counts is plotted along the ordinate.

The present invention provides an improved zeolitic material in particular relative to its use in specific catalytic applications and in particular for the conversion of oxygenates to olefins. Furthermore, provided is an improved process for the conversion of oxygenates to olefins.

Thus, it has quite surprisingly been found that unexpected synergistic effects may be achieved in specific zeolitic materials having particular characteristics, in particular with respect to the size distribution of their primary particles when such specific zeolitic materials are employed in conjunction with one or more alkaline earth metal elements. In this respect, it has quite unexpectedly been found that particular zeolitic materials as these may be obtained from an alkali-free synthetic procedure display technical effects when used in combination with one or more alkaline earth metals which clearly indicate a strong synergy which may not have been expected from the technical, and, in particular, the chemical characteristics of the aforementioned particular features of a zeolitic material when considered by themselves. More specifically, it has quite surprisingly been found that such zeolitic materials as described in the present invention lead to a considerable improvement in catalytic applications and in particular in processes for the conversion of oxygenates to olefins in particular with respect to the catalyst life time when employed in such a process.

Therefore, the present invention relates to a process for the production of a zeolitic material having an MFI, MEL, and/or MWW-type framework structure comprising $YO_2$ and $X_2O_3$, wherein said process comprises (1) preparing a mixture comprising one or more sources for $YO_2$, one or more sources for $X_2O_3$, and one or more solvents;

(2) crystallizing the mixture obtained in step (1) to obtain a zeolitic material having an MFI, MEL, and/or MWW-type framework structure; and (3) impregnating the zeolitic material obtained in step (2) with one or more elements selected from the group of alkaline earth metals;

wherein Y is a tetravalent element, and X is a trivalent element, and wherein the mixture crystallized in step (2) contains 3 wt.-% or less of one or more elements M based on 100 wt.-% of $YO_2$, wherein M stands for sodium.

According to the inventive process, one or more sources for $YO_2$ are provided in step (1). In principle, said one or more sources may be provided in any conceivable form provided that a zeolitic material having an MFI, MEL, and/or MWW-type framework structure comprising $YO_2$ can be crystallized in step (2). Specifically, $YO_2$ is provided as such and/or as a compound which comprises $YO_2$ as a chemical moiety and/or as a compound which (partly or entirely) is chemically transformed to $YO_2$ during the inventive process.

As regards $YO_2$ and/or precursors thereof employed in the inventive process, there is no particular restriction as to the one or more elements for which Y stands, provided that said element is a tetravalent element and that it is comprised in the zeolitic material having an MFI, MEL, and/or MWW-type framework structure crystallized in step (2). In particular, within the meaning of the present invention, $YO_2$ is at least partially and, in some embodiments, entirely comprised in the MFI, MEL, and/or MWW-type framework structure of the zeolitic material as structure-building element, as opposed to non-framework elements which can be present in the pores and cavities formed by the framework structure and typical for zeolitic materials in general. Thus, taking into account the afore-mentioned, Y may stand for any conceivable tetravalent element, Y standing either for a single or several tetravalent elements. In one or more embodiments, tetravalent elements according to the present invention include Si, Sn, Ti, Zr, Ge, as well as any mixture of two or more thereof. According to specific embodiments of the present invention, Y stands for Si.

Therefore, in one or more embodiments, Y is selected from the group consisting of Si, Sn, Ti, Zr, Ge, and mixtures of two or more thereof, Y specifically being Si.

In specific embodiments of the present invention, wherein Y stands for Si or for a combination of Si with one or more further tetravalent elements, the source for SiO$_2$ specifically provided in step (1) can also be any conceivable source. Thus, by way of example, any type of silicas and/or silicates and/or silica derivatives may be used, wherein, in one or more embodiments, the one or more sources for YO$_2$ comprises one or more compounds selected from the group consisting of fumed silica, silica hydrosols, reactive amorphous solid silicas, silica gel, silicic acid, water glass, sesquisilicate, disilicate, colloidal silica, pyrogenic silica, silicic acid esters, or mixtures of any two or more of the afore-mentioned compounds may equally be used. Alternatively, or in addition to one or more of the aforementioned sources of SiO$_2$, elemental silicon may also be employed. According to particularly specific embodiments, the one or more sources for YO$_2$ used in step (1) of the inventive process are selected from the group consisting of fumed silica, silica hydrosols, reactive amorphous solids, reactive amorphous sold silicas, silica gel, colloidal silica, pyrogenic silica, tetraalkoxy silanes, including mixtures of any two or more thereof. According to said particularly specific embodiments, it is further specific that the one or more sources for YO$_2$ are selected from the group consisting of fumed silica, reactive amorphous solid silicas, silica gel, pyrogenic silica, tetraalkoxy silanes, and mixtures of two or more thereof, wherein more specifically the one or more sources for YO$_2$ are selected from the group consisting of fumed silica, tetraalkoxy silanes, as well as mixtures of two or more thereof, wherein even more specifically according to the inventive process, the one or more sources for YO$_2$ comprises one or more tetraalkoxy silanes.

As regards the silicic acid esters which may be used according to particular and specific embodiments of the present invention, said one or more esters specifically have the composition $$Si(OR)_{4-x}(OR')_x$$

wherein x is 0, 1, 2, 3 or 4, may be used as SiO$_2$ source, where R and R' may be different from one another and may each be hydrogen, $C_1$-$C_8$-alkyl, for example methyl, ethyl, n-propyl, isopropyl, n-butyl, isobutyl, tert-butyl, pentyl, hexyl, heptyl or octyl, $C_4$-$C_8$-cycloalkyl, such as cyclobutyl, cyclopentyl, cyclohexyl, cycloheptyl or cyclooctyl, aryl, alkylaryl or arylalkyl, or where R and R' may be identical and may each be hydrogen, $C_1$-$C_8$-alkyl, for example methyl, ethyl, n-propyl, isopropyl, n-butyl, isobutyl, tert-butyl, pentyl, hexyl, heptyl or octyl, $C_4$-$C_8$-cycloalkyl, such as cyclobutyl, cyclopentyl, cyclohexyl, cycloheptyl or cyclooctyl, aryl, alkylaryl or arylalkyl.

According to a specific embodiment of the process according to the present invention, the one or more sources for YO$_2$ and in particular for SiO$_2$ comprises a compound of the general composition $$Si(OR)_4$$

or of the general composition $$Si(OR)_3(OR')$$

where R' is hydrogen and R is $C_1$-$C_8$-alkyl, for example methyl, ethyl, n-propyl, isopropyl, n-butyl, isobutyl, tert-butyl, pentyl, hexyl, heptyl or octyl.

According to particularly specific embodiments wherein the one or more sources for YO$_2$ and in particular for SiO$_2$ comprises one or more tetraalkoxysilanes, it is further specific that said one or more sources comprises one or more compounds of the general composition $$Si(OR)_4$$

wherein R is $C_1$-$C_8$-alkyl, for example methyl, ethyl, n-propyl, isopropyl, n-butyl, isobutyl, tert-butyl, pentyl, hexyl, heptyl or octyl, more specifically methyl, ethyl, n-propyl, isopropyl, n-butyl, isobutyl or tert-butyl, more specifically methyl, ethyl, n-propyl or isopropyl, more specifically methyl or ethyl, particularly specifically ethyl.

According to the present invention, the mixture provided in step (1) further comprises one or more sources for X$_2$O$_3$, wherein X is a trivalent element. As regards the elements which may be employed as the trivalent element X comprised in the one or more sources for X$_2$O$_3$ provided in step (1), there is no particular restriction according to the present invention as to which elements or element mixtures may be employed, provided that a zeolitic material having an MFI, MEL, and/or MWW-type framework structure comprising YO$_2$ and X$_2$O$_3$ as framework elements may be obtained by crystallization in step (2). According to specific embodiments of the present invention, X is selected from the group consisting of Al, B, In, Ga, and mixtures of two or more thereof, wherein specifically X is Al and/or B. According to particularly specific embodiments of the present invention, X comprises Al, wherein even more specifically X is Al. As for YO$_2$ comprised in the zeolitic material having an MFI, MEL, and/or MWW-type framework structure, within the meaning of the present invention, X$_2$O$_3$ is also at least partially and specifically entirely comprised in the framework structure of the zeolitic material as structure-building element as opposed to non-framework elements which can be present in the pores and cavities formed by the framework structure and typical for zeolitic materials in general.

Therefore, in one or more embodiments, X is selected from the group consisting of Al, B, In, Ga, and mixtures of two or more thereof, X specifically being Al and/or Ga, and more specifically being Al.

According to particularly specific embodiments of the present invention, wherein X stands for Al or for a combination of Al with one or more further trivalent elements, the source for Al$_2$O$_3$ specifically provided in step (1) can also be any conceivable source. In principle, any conceivable compounds which permit the preparation of the zeolitic material according to the present invention may be used as the aluminum source. Thus, by way of example, the one or more sources for Al$_2$O$_3$ may comprise one or more compounds selected from aluminum, aluminum alkoxides, alumina, aluminates, and aluminum salts. In the process according to the present invention, the use of aluminum nitrate, aluminum sulfate or a trialkoxyaluminate of the composition Al(OR)$_3$ or a mixture of two or more of these compounds as aluminum source is particularly specific. Regarding the trialkoxyaluminates of the composition Al(OR)$_3$, the radicals R may be identical or different from one another and are $C_1$-$C_8$-alkyl, for example methyl, ethyl, n-propyl, isopropyl, n-butyl, isobutyl, tert-butyl, pentyl, hexyl, heptyl or octyl, $C_4$-$C_8$-cycloalkyl, such as cyclobutyl, cyclopentyl, cyclohexyl, cycloheptyl or cyclooctyl, aryl, alkylaryl or arylalkyl. According to particularly specific embodiments of the process according to the present invention, the aluminum source used is aluminum sulfate. As regards the aluminum salts specifically employed, these may be used in their dehydrated form and/or as one or more hydrates or hydrated forms thereof.

As regards the amount in which the one or more sources for YO$_2$ and X$_2$O$_3$ may be provided in step (1) of the inventive process, no particular restriction applies provided that a zeolitic material having an MFI, MEL, and/or MWW-type framework structure comprising YO$_2$ and X$_2$O$_3$ may be crystallized in step (2). Same applies accordingly with respect to the relative amounts of the one or more sources for $YO_2$ and $X_2O_3$ which may be employed for preparing the mixture in step (1) such that in principle, no particular restriction applies with respect to the $YO_2:X_2O_3$ molar ratio which may be calculated for the mixture prepared in step (1) based on the respective amounts of the one or more sources for $YO_2$ and $X_2O_3$. Thus, by way of example, relative to the amount of the one or more sources for $YO_2$ provided in the mixture of step (1), the $YO_2:X_2O_3$ molar ratio of the mixture may range anywhere from 10 to 1,500, wherein specifically molar ratios are provided comprised in the range of from 30 to 1,200, more specifically from 50 to 900, more specifically from 70 to 700, more specifically from 80 to 500, and even more specifically of from 90 to 300. According to particularly specific embodiments, the $YO_2:X_2O_3$ molar ratio of the mixture provided in step (1) is comprised in the range of from 100 to 250.

Therefore, in one or more embodiments, the $YO_2:X_2O_3$ molar ratio of the mixture prepared in step (1) ranges from 10 to 1,500, specifically from 30 to 1,200, more specifically from 50 to 900, more specifically from 70 to 700, more specifically from 80 to 500, more specifically from 90 to 300, and even more specifically from 100 to 250.

According to alternatively specific embodiments of the inventive process, however, the $YO_2:X_2O_3$ molar ratio of the mixture may range anywhere from 10 to 300, wherein specifically molar ratios are provided comprised in the range of from 30 to 220, more specifically from 50 to 180, more specifically from 70 to 150, more specifically from 90 to 120, and even more specifically of from 95 to 105. According to further embodiments of the inventive process which are alternatively specific, the $YO_2:X_2O_3$ molar ratio of the mixture may range anywhere from 50 to 500, wherein specifically molar ratios are provided comprised in the range of from 100 to 400, more specifically from 150 to 350, more specifically from 200 to 300, more specifically from 220 to 280, and even more specifically of from 240 to 260.

According to the inventive process, the mixture provided in step (1) further comprises one or more solvents. In principle, there is no particular restriction according to the present invention neither with respect to the type and/or number of the one or more solvents, nor with respect to the amount in which they may be used in the inventive process provided that a zeolitic material having an MFI, MEL, and/or MWW-type framework structure may be crystallized in step (2). According to one or more embodiments, the one or more solvents comprise one or more polar solvents, wherein the one or more polar solvents are selected from the group consisting of alkanols, water, and mixtures of two or more thereof. According to particularly specific embodiments, the one or more solvents comprise one or more polar solvents selected from the group consisting of methanol, ethanol and/or propanol, iso-propanol, water, and mixtures of two or more thereof, and more specifically from the group consisting of methanol, ethanol, water, and mixtures of two or more thereof. According to specific embodiments, the one or more solvents and, in particular, the one or more polar solvents comprise water, and more specifically, distilled water, wherein according to particularly specific embodiments distilled water is used as the only solvent in the mixture provided in step (1) and crystallized in step (2).

Therefore, in one or more embodiments, the one or more solvents comprise one or more polar solvents, wherein the one or more polar solvents are specifically selected from the group consisting of alkanols, water, and mixtures of two or more thereof.

In the inventive process, the mixture prepared according to step (1) is subsequently crystallized in step (2), wherein said mixture crystallized in step (2) contains 3 wt.-% or less of one or more elements M based on 100 wt.-% of $YO_2$. In general, M stands for sodium which may be present in the mixture prepared in step (1) and crystallized in step (2) of the inventive process. According to specific embodiments of the inventive process, the mixture crystallized in step (2) contains 3 wt.-% or less of both sodium and potassium based on 100 wt.-% of $YO_2$, M accordingly standing for sodium and potassium. According to particularly specific embodiments of the inventive process, however, the mixture prepared in step (1) and crystallized in step (2) also does not contain any further alkali metal elements besides sodium and potassium in an amount wherein the total amount of alkali metal elements in the mixture provided in step (1) would not exceed 3 wt.-% based on 100 wt.-% of $YO_2$. Accordingly, according to said particularly specific embodiments, the mixture provided in step (1) and crystallized in step (2) contains 3 wt.-% or less of alkali metal elements, wherein it is further specific that said mixture contains 3 wt.-% or less of both alkali and alkaline earth metal elements.

Therefore, according to specific embodiments of the inventive process, M stands for sodium and potassium, and specifically for the group of alkali metals, wherein more specifically M stands for the group of alkali and alkaline earth metals.

According to embodiments of the present invention which are further specific, the mixture provided in step (1) and crystallized in step (2) contains less than 1 wt.-% of one or more elements M according to any of the particular or specific embodiments of the present invention based on 100 wt.-% of $YO_2$, and more specifically 0.5 wt.-% or less of one or more elements M based on 100 wt.-% of $YO_2$, more specifically 0.1 wt.-% or less, more specifically 0.05 wt.-% or less, more specifically 0.01 wt.-% or less, more specifically 0.005 wt.-% or less, more specifically 0.001 wt.-% or less and more specifically 0.0005 wt.-% or less. According to embodiments thereof, the mixture provided in step (1) and crystallized in step (2) contains 0.0003 wt.-% or less of one or more elements M based on 100 wt.-% of $YO_2$, wherein it is yet further specific that the mixture crystallized in step (2) of the inventive process contains less than 0.0001 wt.-% of one or more elements M therein and is therefore substantially free of the one or more elements M according to any of the particular or specific embodiments of the present invention.

According to specific embodiments of the present invention, the mixture provided in step (1) and crystallized in step (2) further comprises one or more organotemplates. In principle, according to the present invention, there is no particular restriction neither with respect to the number nor with respect to the type of the one or more organotemplates which may be used therein provided that a zeolitic material having an MFI, MEL, and/or MWW-type framework structure is crystallized in step (2) from the mixture obtained in step (1). It is, however, specific according to the present invention that the one or more organotemplates comprise one or more compounds selected from the group consisting of tetraalkylammonium and alkenyltrialkylammonium compounds. As regards the alkyl moieties which may be comprised in the tetraalkylammonium and alkenyltrialkylammonium compounds, again no particular restriction applies in this respect provided that a zeolitic material having an MFI, MEL, and/or MWW-type framework structure may be crystallized in step (2). Accordingly, any conceivable alkyl moieties including combinations of two or more alkyl moieties may be contained in the respective one or more tetraalkylammonium and/or one or more alkenyltrialkylammonium compounds wherein specifically the alkyl moieties are selected from the group consisting of $C_1$-$C_8$-alkyl, more specifically from the group consisting of $C_1$-$C_6$-alkyl, more specifically $C_1$-$C_5$-alkyl, and more specifically from the group consisting of $C_1$-$C_4$-alkyl. According to particularly specific embodiments of the present invention, the alkyl moieties respectfully comprised in the one or more tetraalkylammonium and/or alkenyltrialkylammonium compounds is selected from the group consisting of $C_1$-$C_3$-alkyl.

As concerns the alkenyl moiety contained in the alkenyltrialkylammonium cation of the one or more alkenyltrialkylammonium compounds specifically comprised among the one or more organotemplates, again, no particular restriction applies in this respect provided that a zeolitic material having an MFI, MEL, and/or MWW-type framework structure may be crystallized in step (2). According to particularly specific embodiments of the present invention, however, the alkenyl moiety of the alkenyltrialkylammonium cation is selected from the group consisting of $C_2$-$C_6$-alkenyl, more specifically from the group consisting of $C_2$-$C_5$-alkenyl, more specifically $C_2$-$C_4$-alkenyl, and even more specifically from the group consisting of $C_2$-$C_3$-alkenyl. According to particularly specific embodiments thereof, the alkenyl moiety of the alkenyltrialkylammonium cation comprised in the one or more alkenyltrialkylammonium compounds specifically comprised among the one or more organotemplates is 2-propene-1-yl, 1-propene-1-yl, or 1-propene-2-yl, wherein according to particularly specific embodiments thereof, the alkenyl moiety is 2-propene-1-yl or 1-propene-1-yl.

Therefore, in one or more embodiments, the mixture in step (1) further comprises one or more organotemplates, the one or more organotemplates specifically comprising one or more compounds selected from the group consisting of tetraalkylammonium and alkenyltrialkylammonium compounds.

According to yet further specific embodiments of the inventive process, wherein the one or more organotemplates specifically comprised in the mixture prepared in step (1) comprises one or more tetraalkylammonium compounds, it is specific that said compounds are selected from the group consisting of tetraethylammonium compounds, triethylpropylammonium compounds, diethyldipropylammonium compounds, ethyltripropylammonium compounds, tetrapropylammonium compounds, and mixtures of two or more thereof, wherein the one or more organotemplates comprises one or more tetrapropylammonium compounds.

Likewise, as regards particularly specific embodiments of the present invention wherein the one or more organotemplates specifically comprised in the mixture prepared in step (1) comprise one or more alkenyltrialkylammonium compounds, these are selected from the group consisting of N—($C_2$-$C_5$)-alkenyl-tri-($C_1$-$C_5$)-alkylammonium compounds, and more specifically are selected from the group consisting of N—($C_2$-$C_4$)-alkenyl-tri-($C_1$-$C_4$)-alkylammonium compounds, more specifically from the group consisting of N—($C_2$-$C_3$)alkenyl-tri-($C_2$-$C_4$)alkylammonium compounds, wherein even more specifically these are selected from the group consisting of N-(2-propene-1-yl)-tri-n-propylammonium compounds, N-(1-propene-1-yl)-tri-n-propylammonium compounds, N-(1-propene-2-yl)-tri-n-propylammonium compounds, including mixtures of two or more thereof. According to particularly specific embodiments thereof, the one or more alkenyltrialkylammonium compounds specifically comprised in the mixture prepared in step (1) is selected from the group consisting of N-(2-propene-1-yl)-tri-n-propylammonium compounds, N-(1-propene-1-yl)-tri-n-propylammonium compounds, and mixtures of two or more thereof.

As regards the one or more tetraalkylammonium and/or alkenyltrialkylammonium compounds further added to the mixture prepared in step (1) according to particularly specific embodiments of the inventive process, said one or more compounds are accordingly provided in the form of a salt. As regards the counterion to the one or more tetraalkylammonium and/or alkenyltrialkylammonium cations contained in said one or more compounds, again no particular restriction applies according to the present invention provided that an MFI, MEL, and/or MWW-type framework structure may be crystallized in step (2) of the inventive process. Thus, any conceivable counterion to said one or more cations may be employed for providing the one or more tetraalkylammonium and/or alkenyltrialkylammonium compounds. Thus, by way of example, the one or more counterions to the one or more tetraalkylammonium and/or alkenyltrialkylammonium salts may comprise one or more anions selected from the group consisting of chloride, fluoride, bromide, carbonate, hydrogen carbonate, hydroxide, nitrate, phosphate, hydrogen phosphate, dihydrogen phosphate, sulfate, hydrogen sulfate, acetate, formate, oxalate, cyanate, and mixtures of two or more thereof, more specifically from the group consisting of chloride, fluoride, bromide, hydrogen carbonate, hydroxide, nitrate, dihydrogen phosphate, hydrogen sulfate, acetate, formate, oxalate, and combinations of two or more thereof, wherein even more specifically the one or more counterions comprise one or more anions selected from the group consisting of chloride, bromide, hydroxide, nitrate, and combinations of two or more thereof.

According to particularly specific embodiments of the present invention, the one or more tetraalkylammonium and/or alkenyltrialkylammonium salts added to the mixture prepared in step (1) and crystallized in step (2) of the inventive process are, independently from one another, a hydroxide and/or a halide salt, and more specifically a salt selected from the group consisting of hydroxide, chloride, bromide, and mixtures of two or more thereof, wherein even more specifically the salts comprise one or more hydroxides. Thus, according to particularly specific embodiments of the present invention, wherein the one or more organotemplates comprises one or more tetraalkylammonium compounds, said one or more organotemplates comprises tetrapropylammonium hydroxide and/or chloride, and even more specifically tetrapropylammonium hydroxide. Likewise, according to particularly specific embodiments of the present invention, wherein the one or more organotemplates specifically added to the mixture prepared in step (1) comprises one or more alkenyltrialkylammonium compounds, the one or more organotemplates comprises N-(2-propene-1-yl)-tri-n-propylammonium and/or N-(1-propene-1-yl)-tri-n-propylammonium hydroxide and/or chloride, and even more specifically N-(2-propene-1-yl)-tri-n-propylammonium hydroxide and/or N-(1-propene-1-yl)-tri-n-propylammonium hydroxide.

As regards the amount in which the one or more organotemplates are specifically comprised in the mixture prepared in step 1 of the inventive process according to which one or more organotemplates are specifically provided for crystallizing a zeolitic material having an MFI, MEL, and/or MWW-type framework structure, no particular restriction applies. Thus, by way of example, the molar ratio of the total amount of the one or more organotemplates of the mixture obtained in step (1) to $YO_2$ may range anywhere from 1:0.1-1:30, wherein specifically the molar ratio ranges from 1:0.5-1:20, more specifically from 1:1-1:15, more specifically from 1:3-1:10, and more specifically from 1:4-1:7. According to particularly specific embodiments thereof, the molar ratio of the total amount of the one or more organotemplates to $YO_2$ ranges from 1:5-1:5.6.

Therefore, in one or more embodiments, the molar ratio of the total amount of the one or more organotemplates of the mixture obtained in step (1) to $YO_2$ ranges from 1:(0.1-30), specifically from 1:(0.5-20), more specifically from 1:(1-15), more specifically from 1:(3-10), from 1:(4-7), and even more specifically from 1:(5-5.6).

According to the inventive process, it is further specific that the mixture according to step (1) comprises one or more sources for $OH^-$ for crystallizing an MFI, MEL, and/or MWW-type framework structure in step (2) of the inventive process. As regards the particular type of source or sources for $OH^-$ which may be employed in the inventive process, no particular restriction applies provided that $OH^-$ anions may be directly and/or indirectly generated in the mixture prepared in step (1) and crystallized in step (2) of the inventive process. Within the meaning of the present invention, $OH^-$ anions are indirectly provided by any chemical reaction leading to the generation of $OH^-$ anions such as e.g. a reaction of a Lewis base with water, wherein a protonated form of the base and $OH^-$ are generated by chemical reaction of the former.

According to the present invention, the one or more sources for $OH^-$ specifically further comprised in the mixture according to step (1) specifically comprise one or more sources directly containing $OH^-$ and in particular one or more Bronsted bases, wherein even more specifically said one or more sources for $OH^-$ comprise one or more hydroxides of an organotemplate salt further comprised in the mixture prepared in step (1) according to any of the particular or specific embodiments of the present invention. Thus, according to a particularly specific embodiment thereof, said one or more sources for $OH^-$ specifically comprise one or more hydroxides selected from the group consisting of tetraalkylammonium and/or alkenyltrialkylammonium hydroxides, and more specifically one or more hydroxides selected from the group consisting of tetraethylammonium hydroxide, triethylpropylammonium hydroxide, diethyldipropylammonium hydroxide, ethyltripropylammonium hydroxide, tetrapropylammonium hydroxide, N-(2-propene-1-yl)-tri-n-propylammonium hydroxide, N-(1-propene-1-yl)-tri-n-propylammonium hydroxide, N-(1-propene-2-yl)-tri-n-propylammonium hydroxide, and mixtures of two or more thereof, wherein even more specifically the one or more hydroxides are selected from the group consisting of tetrapropylammonium hydroxide, N-(2-propene-1-yl)-tri-n-propylammonium hydroxide, N-(1-propene-1-yl)-tri-n-propylammonium hydroxide, and mixtures of two or more thereof. According to particularly specific embodiments thereof, the one or more sources for $OH^-$ comprise tetrapropylammonium hydroxide, wherein even more specifically the one or more sources for $OH^-$ is tetrapropylammonium hydroxide.

Therefore, in one or more embodiments, the mixture according to step (1) further comprises one or more sources for $OH^-$, wherein said one or more sources for $OH^-$ specifically comprises a hydroxide of an organotemplate salt, more specifically one or more hydroxides selected from the group consisting of tetraalkylammonium and/or alkenyltrialkylammonium hydroxides.

As concerns the amount of $OH^-$ which may be comprised in the mixture prepared in step (1) of the inventive process, no particular restriction applies according to the present invention provided that a zeolitic material having MFI, MEL, and/or MWW-type framework structure may be crystallized in step (2) of the inventive process. Thus, by way of example, the $OH^-$:$YO_2$ molar ratio of the mixture obtained in step (1) according to said specific embodiments may range anywhere from 0.01 to 5, wherein specifically the $OH^-$:$YO_2$ molar ratio ranges from 0.05 to 2, more specifically from 0.1 to 1, more specifically from 0.12 to 0.5, and more specifically from 0.15 to 0.3. According to particularly specific embodiments of the present invention, the $OH^-$:$YO_2$ molar ratio of the mixture obtained in step (1) according to particular embodiments of the present invention ranges from 0.18 to 0.2.

In step (1) according to the present invention, the mixture can be prepared by any conceivable means, wherein mixing by agitation is specific, specifically by means of stirring.

As regards the crystallization performed in step (2) of the inventive process, no particular restriction applies according to the present invention as to the actual means employed for allowing the crystallization of a zeolitic material having an MFI, MEL, and/or MWW-type framework structure from the mixture obtained in step (1). Thus, any suitable means may be employed, wherein it is specific that the crystallization is achieved by heating of the mixture of step (1). According to said specific embodiments, no particular restriction again applies with respect to the temperature at which said crystallization in step (2) may be achieved, wherein it is specific that the crystallization is conducted under heating at a temperature comprised in the range of from 80 to 250° C., more specifically from 100 to 220° C., more specifically from 120 to 200° C., more specifically from 140 to 180° C., and more specifically from 145 to 175° C. According to particularly specific embodiments of the present invention, the specific heating of the mixture provided in step (1) in step (2) for the crystallization of a zeolitic material having an MFI, MEL, and/or MWW-type framework structure is conducted at a temperature comprised in the range of from 150 to 170° C.

Concerning the heating specifically employed at step (2) of the inventive process as means for the crystallization of the zeolitic material having an MFI, MEL, and/or MWW-type framework structure, said heating may in principle be conducted under any suitable pressure provided that crystallization is achieved. In specific embodiments of the present invention, the mixture according to step (1) is subjected in step (2) to a pressure which is elevated with regard to normal pressure. The term "normal pressure" as used in the context of the present invention relates to a pressure of 101,325 Pa in the ideal case. However, this pressure may vary within boundaries known to the person skilled in the art. By way of example, this pressure can be in the range of from 95,000 to 106,000 or of from 96,000 to 105,000, or of from 97,000 to 104,000, or of from 98,000 to 103,000, or of from 99,000 to 102,000 Pa.

In specific embodiments of the inventive process, wherein a solvent is present in the mixture according to step (1), it is furthermore specific that heating in step (2) is conducted under solvothermal conditions, meaning that the mixture is crystallized under autogenous pressure of the solvent which is used. This may for example be conducted by heating the mixture obtained in step (1) in an autoclave or other crystallization vessel suited for generated solvothermal conditions. In particularly specific embodiments, wherein the solvent comprises water, and specifically distilled water, heating in step (2) is accordingly specifically conducted under hydrothermal conditions.

The apparatus which can be used in the present invention for crystallization is not particularly restricted, provided that the desired parameters for the crystallization process can be realized, in particular with respect to the specific embodiments requiring particular crystallization conditions. In the specific embodiments conducted under solvothermal conditions, any type of autoclave or digestion vessel can be used.

Furthermore, as regards the period in which the specific heating in step (2) of the inventive process is conducted for crystallizing the zeolitic material, there is again no particular restriction in this respect provided that the period of heating is suitable for achieving crystallization of a zeolitic material having an MFI, MEL, and/or MWW-type framework structure. Thus, by way of example, heating may be performed for a period of at least 3 hours, wherein specifically the period of heating may range anywhere from 6 hours to 15 days, more specifically from 9 hours to 10 days, more specifically from 12 hours to 7 days, more specifically from 15 hours to 5 days, more specifically from 18 hours to 4 days, and more specifically from 21 hours to 3 days. According to particularly specific embodiments, heating in step (2) of the inventive process is conducted for a period of from 1 to 2 days.

According to specific embodiments of the present invention, wherein the mixture is heated in step (2), said heating may be conducted during the entire crystallization process or during only one or more portions thereof, provided that a zeolitic material is crystallized. Specifically, heating is conducted during the entire duration of crystallization.

Further regarding the means of crystallization in step (2) of the inventive process, it is principally possible according to the present invention to perform said crystallization either under static conditions or by means of agitating the mixture. According to embodiments involving the agitation of the mixture, there is no particular restriction as to the means by which said agitation may be performed such that any one of vibrational means, rotation of the reaction vessel, and/or mechanical stirring of the reaction mixture may be employed to this effect wherein according to said embodiments it is specific that agitation is achieved by stirring of the reaction mixture. According to alternatively specific embodiments, however, crystallization is performed under static conditions, i.e. in the absence of any particular means of agitation during the crystallization process.

In general, the process of the present invention can optionally comprise further steps for the work-up and/or further physical and/or chemical transformation of the zeolitic material crystallized in step (2) from the mixture provided in step (1), wherein said work up steps are conducted prior to step (3) of impregnating the zeolitic material. The crystallized material can for example be subject to any sequence of isolation and/or washing procedures, wherein the zeolitic material obtained from crystallization in step (2) is specifically subject to at least one isolation and at least one washing procedure.

Isolation of the crystallized product can be achieved by any conceivable means. Specifically, isolation of the crystallized product can be achieved by means of filtration, ultrafiltration, diafiltration, centrifugation and/or decantation methods, wherein filtration methods can involve suction and/or pressure filtration steps. According to specific embodiments, it is specific that the reaction mixture is first adjusted to a pH comprised in the range of from 5 to 9, specifically of 6 to 8, more specifically of 6.5 to 7.8, and more specifically of 7 to 7.6 prior to isolation. Within the meaning of the present invention, pH values specifically refer to those values as determined via a standard glass electrode.

With respect to one or more optional washing procedures, any conceivable solvent can be used. Washing agents which may be used are, for example, water, alcohols, such as methanol, ethanol or propanol, or mixtures of two or more thereof. Examples of mixtures are mixtures of two or more alcohols, such as methanol and ethanol or methanol and propanol or ethanol and propanol or methanol and ethanol and propanol, or mixtures of water and at least one alcohol, such as water and methanol or water and ethanol or water and propanol or water and methanol and ethanol or water and methanol and propanol or water and ethanol and propanol or water and methanol and ethanol and propanol. Water or a mixture of water and at least one alcohol, specifically water and ethanol, is specific, distilled water being very particularly specific as the only washing agent.

Specifically, the separated zeolitic material is washed until the pH of the washing agent, specifically the washwater, is in the range of from 6 to 8, specifically from 6.5 to 7.5.

Furthermore, the inventive process can optionally comprise one or more drying steps. In general, any conceivable means of drying can be used. In general the drying procedure may include any suitable stationary or continuous drying procedures such as the use of a band dryer. Drymilling and spinflash procedures may also be mentioned as possible alternatives. Drying procedures specifically include heating and/or applying vacuum to the zeolitic material. In envisaged embodiments of the present invention, one or more drying steps may also involve spray drying, such as may be achieved by spray granulation of the zeolitic material.

In embodiments which comprise at least one drying step, the drying temperatures are specifically in the range of from 25° C. to 150° C., more specifically of from 60 to 140° C., more specifically of from 70 to 130° C. and even more specifically in the range of from 75 to 125° C. The durations of drying are specifically in the range of from 2 to 24 h, more specifically in the range of 2.5 to 10 hours, more specifically of from 3 to 7 h, and even more specifically of from 3.5 to 5 h.

According to alternative embodiments of the inventive process which are specific, the zeolitic material crystallized in step (2) is directly subject to at least one step of drying, specifically to spray drying and or spray granulation, without isolating, washing, or drying of the zeolitic material beforehand. Directly subjecting the mixture obtained from step (2) of the inventive process to a spray drying or spray granulation stage has the advantage that isolation and drying is performed in a single stage. Consequently, according to this embodiment of the present invention, an even more specific process is provided wherein not only removal of organotemplate compounds is avoided, but also the number of post-synthesis workup steps is minimized, as a result of which the zeolitic material can be obtained from a highly simplified process.

In general, the optional washing and/or isolation and/or ion-exchange procedures comprised in the inventive process can be conducted in any conceivable order and repeated as often as desired.

In addition to one or more of the aforementioned work-up steps which may be conducted after step (2) and prior to step (3) of the inventive process, according to further specific embodiments, in addition to the one or more optional drying steps or in place of said one or more drying steps, the optionally washed zeolitic material is subject to one or more steps of calcination. According to the present invention, said one or more steps of calcination are particularly specific with respect to particular embodiments of the inventive process, wherein the mixture prepared in step (1) further comprises one or more organotemplates for removing said organotemplates after the synthesis of the zeolitic material having an MFI, MEL, and/or MWW-type framework structure. According to said specific embodiments wherein one or more calcination steps are performed after step (2) and prior to step (3) of the inventive process, no particular restriction applies neither with respect to the repetition and in particular the number of repetitions of the calcination step which may be performed, nor with respect to the temperature employed in the calcination procedure nor with respect to the duration of the calcination procedure. According to the particular embodiments of the inventive process, wherein one or more organotemplates are further comprised in the mixture prepared in step (1), it is specific that the conditions of the calcination and in particular the temperature and/or duration and/or number of repetitions of the calcination step is chosen such that the one or more organotemplates are substantially removed from the porous structure of the zeolitic material having an MFI, MEL, and/or MWW-type framework structure.

Within the meaning of the present invention, the term "substantially" and in particular the use of said term with respect to the amount of said one or more organotemplates which may at most remain in the porous structure of the zeolitic material after calcination thereof designates residual amounts of carbon and/or nitrogen originating from said one or more organotemplates which may at most remain in the porous structure of the zeolitic material. More specifically, a zeolitic material having been crystallized in step (2) of the inventive process in the presence of one or more organotemplates is substantially free thereof within the meaning of the present invention in cases where the carbon and/or nitrogen content thereof is of 1.0 wt.-% or less based on 100 wt.-% of $YO_2$ contained in the framework structure of the zeolitic material having an MFI, MEL, and/or MWW-type framework structure, and specifically an amount of 0.5 wt.-% or less, more specifically of 0.2 wt.-% or less, more specifically of 0.1 wt.-% or less, more specifically of 0.05 wt.-% or less, more specifically of 0.01 wt.-% or less, more specifically of 0.005 wt.-% or less, and more specifically of 0.001 wt.-% or less based on 100 wt.-% of $YO_2$ in the zeolitic material.

As regards the one or more calcination steps according to specific embodiments of the inventive process, the temperature of the calcination procedure employed in the inventive process may range anywhere from 300 to 850° C., wherein specifically the calcination in step (2d) ranges from 350 to 700° C., and more specifically from 400 to 600° C. According to particularly specific embodiments of the inventive process, the calcination in step (2d) is conducted at a temperature in the range of 450 to 550° C. As regards the duration of the one or more calcination steps according to step (2d) of the inventive process, there is again no particular restriction in this respect such that the calcination may be conducted for a duration ranging anywhere from 1 to 80 hours, wherein specifically the duration of the calcination according to any of the particular and specific embodiments described in the present application ranges from 2 to 24 h during which the temperature of calcination is maintained, more specifically from 2.5 to 12 h, more specifically from 3 to 10 h, more specifically from 3.5 to 8 h, and more specifically from 4 to 7 h. According to particularly specific embodiments of the inventive process further comprising a calcination procedure, the duration thereof ranges from 4.5 to 6 h, during which the chosen temperature of calcination is maintained.

As regards the number of times the calcination procedure in step (2d) may be performed, it is specific that the calcination procedure is conducted one to three times in step (2d), wherein more specifically the calcination procedure is conducted once or twice, wherein according to particularly specific embodiments the calcination procedure is performed once in step (2d) of the inventive process.

According to the present invention it is further specific that the zeolitic material is subject to a hydrothermal treatment step (2e). In general, there is no particular restriction as to how the hydrothermal treatment is conducted, provided that the treatment leads to a change in the zeolitic materials physical and/or chemical properties, wherein the hydrothermal treatment leads to a reduction in the zeolitic material's hydrophobicity.

Thus, in principle, the specific hydrothermal treatment step may be conducted under any suitable conditions, and in particular any suitable pressure and temperature. According to the present invention it is however specific that the hydrothermal treatment is conducted under autogenous pressure, which may for example be achieved by using an autoclave or any suitable pressure digestion vessel.

As regards the temperature at which the hydrothermal treatment in step (2e) is conducted, again, any suitable temperature may be employed, wherein it is specific that the hydrothermal treatment in step (2e) is conducted under heating, and specifically at a temperature ranging from 80 to 250° C., more specifically from 100 to 220° C., more specifically from 120 to 200° C., more specifically from 140 to 190° C., and more specifically from 160 to 185° C. According to the present invention it is however particularly specific that the hydrothermal treatment in step (2e) is conducted at a temperature comprised in the range of from 170 to 180° C.

With respect to the duration of the hydrothermal treatment step, and in particular the duration of heating according to any of the specific and particularly embodiments of the inventive process, again no particular restriction applies provided that the duration is sufficient for leading to a change in the zeolitic material's physical and/or chemical properties and in particular to it's hydrophobicity under that chosen conditions, in particular with respect to the chosen temperature and pressure. Thus, by way of example, the duration of the hydrothermal treatment may range anywhere from 2 to 72 h, wherein specifically the treatment in step (2e) is conducted for a duration ranging from 4 to 48 h, more specifically from 8 to 36 h, and more specifically from 12 to 30 h. According to the present invention the hydrothermal treatment in step (2e) is conducted for a period ranging from 18 to 24 h.

Concerning the effect of the hydrothermal treatment specifically conducted according to step (2e), there is no particular restriction as to the changes in physical and/or chemical properties of the zeolitic material which may be achieved, wherein the conditions of hydrothermal treatment according to the specific and particularly specific embodiments of the inventive process in particular with respect to temperature, pressure, and duration lead to an increase in the zeolitic material's hydrophobicity. Thus, according to the present invention it is specific that the zeolitic material obtained in step (2e) displays a decreased water uptake relative to the zeolitic material prior to the treatment in step (2e). Accordingly, as regards the specific water uptake of the zeolitic material obtained in step (2e), there is in principle no restriction according to the aforementioned specific embodiments of the present invention provided that the zeolitic material's hydrophobicity is increased, i.e. that the water uptake of the zeolitic material decreases as a result of the treatment in step (2e). Thus, in general, the water uptake of the zeolitic material obtained in step (2e) is not particularly restricted, such that the water uptake of the material obtained in said step may by way of example display a water uptake of 10.0 wt.-% or less, wherein specifically the hydrothermally treated zeolitic material obtained in step (2e) specifically displays a water uptake of 7.4 wt.-% or less, more specifically of 6.2 wt.-% or less, more specifically of 6.0 wt.-% or less, more specifically of 5.0 wt.-% or less, more specifically of 4.5 wt.-% or less, more specifically of 4.2 wt.-% or less, more specifically of 3 wt.-% or less, and more specifically of 2.2 wt.-% or less. According to the present invention the hydrothermally treated zeolitic material obtained in step (2e) displays a water uptake of 2 wt.-% or less, and more specifically of 1.5 wt.-% or less.

Within the meaning of the present invention, the water uptake of a material and in particular of a zeolitic material as defined in any of the particular and specific embodiments of the present invention expressed in wt.-% specifically refers to the water uptake of a material at 85 wt.-% relative humidity (RH) expressed in increase in weight compared to the dry sample, i.e. the weight of the sample measured at 0% RH. According to the present invention it is specific that the weight of the sample measured at 0% RH refers to the sample from which residual moisture has been removed by heating the sample to 100° C. (heating ramp of 5° C./min) and holding it for 6 h under a nitrogen flow. According to the present invention the water uptake of a material as defined for any of the particular and specific embodiments of the inventive process refers to the water uptake of a material and in particular of a zeolitic material at 85% RH as obtained according to the procedure for the measurement of the water adsorption/desorption isotherms as described in the experimental section of the present application.

Therefore, in one or more embodiments, after step (2) and prior to step (3) the process further comprises
  (2a) adjusting the pH of the product mixture obtained in (2) to a pH in the range of 5 to 9, specifically of 6 to 8, more specifically of 6.5 to 7.8, and more specifically of 7 to 7.6; and/or
  (2b) isolating the zeolitic material from the product mixture obtained in (2), specifically by filtration, ultrafiltration, diafiltration, centrifugation and/or decantation methods; and/or
  (2c) washing the zeolitic material; and/or
  (2d) drying and/or calcining the zeolitic material;
  (2e) subjecting the zeolitic material to a hydrothermal treatment.

In step (3) of the inventive process, the zeolitic material obtained in step (2) is impregnated with one or more elements selected from the group of alkaline earth metals. As regards the means for impregnation of the zeolitic material which may be employed in the inventive process, no particular restriction applies provided that the one or more elements selected from the group of alkaline earth metals may be effectively provided within the porous structure of the zeolitic material having an MFI, MEL, and/or MWW-type framework structure. Thus, any suitable impregnation method may be employed in step (3) of the inventive process, such as for example impregnation via a procedure involving the soaking of the zeolitic material in a suitable solution and/or suspension of one or more compounds containing the one or more elements selected from the group of alkaline earth metals, as well as by a spray impregnation procedure and/or by means of impregnation by incipient wetness, wherein the afore-mentioned procedures may be used by themselves or in any combination of two or more thereof. According to the present invention, it is, however, particularly specific that the impregnation of the zeolitic material is achieved by spray impregnation thereof.

With respect to the one or more elements selected from the group of alkaline earth metals with which the zeolitic material obtained in step (2) of the inventive process is impregnated, said elements may be employed in any suitable form allowing for their inclusion into the porous structure of the zeolitic material. Thus, said one or more elements may in principle be employed in elemental form and/or in the form of one or more compounds and in particular in the form of one or more salts thereof. According to the inventive process, it is specific that the one or more element selected from the group of alkaline earth metals is employed in the form of one or more salts for impregnation into the zeolitic material. As regards the specific salts of the one or more elements selected from the group of alkaline earth metals which may be employed in step (3), again no particular restriction applies relative to the type or number of different salts which may be employed, wherein specifically the one or more salts of said one or more elements is selected from the group consisting of halides, carbonates, hydroxide, nitrate, phosphates, sulfates, acetate, formate, oxalate, cyanide, and mixtures of two or more thereof, wherein specifically the one or more salts are selected from the group consisting of chloride, fluoride, bromide, hydrogen carbonate, hydroxide, nitrate, hydrogen phosphate, dihydrogen phosphate, hydrogen sulfate, acetate, and mixtures of two or more thereof, wherein more specifically the one or more salts is selected from the group consisting of chloride, bromide, hydroxide, nitrate, acetate, and mixtures of two or more thereof. According to particularly specific embodiments of the inventive process, the one or more salts of the one or more elements selected from the group of alkaline earth metals specifically employed in step (3) for the impregnation of the zeolitic material obtained in step (2) comprises one or more nitrate salts.

Regarding the one or more elements selected from the group of alkaline earth metals employed in step (3), any one or more of said alkaline earth metals may principally be impregnated in the zeolitic material and in particular any combination of two or more alkaline earth metals. According to the inventive process, it is, however, specific that in step (3), the zeolitic material is impregnated with one or more elements selected from the group consisting of Mg, Ca, Ba, Sr, and mixtures of two or more thereof, wherein specifically the zeolitic material is impregnated with Mg and/or Ca, and more specifically with Mg.

Concerning the amount of the one or more elements selected from the group of alkaline earth metals which is impregnated into the zeolitic material obtained in step (2), no particular restriction applies according to the present invention such that any conceivable amount may be impregnated therein. Thus, by way of example, the zeolitic material may be impregnated such that 0.1 to 15 wt.-% of the one or more elements selected from the group of alkaline earth metals calculated as the element is impregnated into the zeolitic material based on the total weight thereof. According to specific embodiments, however, the zeolitic material having an MFI, MEL, and/or MWW-type framework structure is impregnated in step (3) with from 0.5 to 10 wt.-% of the one or more elements selected from the group of alkaline earth metals, more specifically with from 1 to 7 wt.-%, more specifically with from 2 to 5 wt.-%, more specifically with from 3 to 4.5 wt.-%, and more specifically with from 3.5 to 4.3 wt.-%. According to particularly specific embodiments of the inventive process, the zeolitic material obtained in step (2) is impregnated in step (3) with from 3.8 to 4.1 wt.-% of one or more elements selected from the group of alkaline earth metals based on the total weight of the zeolitic material.

In general, the zeolitic material obtained according to the inventive process may be any conceivable zeolitic material having an MFI, MEL, and/or MWW-type framework structure, wherein specifically said zeolitic material formed in step (2) comprises one or more zeolites having the MFI-type framework structure. Among the specific zeolitic materials comprising one or more zeolites having the MFI-type framework structure, there is no particular restriction neither with respect to the type and/or number thereof, nor with respect to the amount thereof in the zeolitic material.

According to embodiments of the inventive process wherein the zeolitic material obtained comprises one or more zeolites having an MWW-type framework structure, there is accordingly no particular restriction neither with respect to the type, nor with respect to the number of zeolites having an MWW-type framework structure which may be contained therein. Thus, by way of example, the one or more zeolites having an MWW-type framework structure which may be obtained according to the inventive process may include one or more zeolites selected from the group consisting of MCM-22, [Ga—Si—O]-MWW, [Ti—Si—O]-MWW, ERB-1, ITQ-1, PSH-3, SSZ-25, and mixtures of two or more thereof, wherein specifically, one or more zeolites which may be employed for the conversion of oxygenates to olefins are comprised in the zeolitic material obtained according to the inventive process, wherein in particular the zeolitic material specifically comprises MCM-22 and/or MCM-36.

Same applies accordingly with respect to the one or more zeolites having an MEL-type framework structure which may be comprised in the zeolitic material obtained according to the inventive process. Thus again, by mere way of example, the one or more zeolites having an MEL-type framework structure which may be comprised in the zeolitic material obtained according to the inventive process may include one or more zeolites selected from the group consisting of ZSM-11, [Si—B—O]-MEL, Bor-D (MFI/MEL-intergrowth), Boralite D, SSZ-46, Silicalite 2, TS-2, and mixtures of two or more thereof. In this case also, it is specific that the one or more zeolites having an MEL-type framework structure may be employed for the conversion of oxygenates to olefins, such that according to a particularly specific embodiment of the inventive process, the zeolitic material obtained comprises ZSM-11.

As mentioned above, however, the zeolitic material obtained according to the inventive process comprised one or more zeolites having an MFI-type framework structure, and in particular zeolites of the MFI-type framework structure which may be employed in the conversion of oxygenates to olefins. Again no particular restriction applies, neither with respect to the type of the one or more zeolites having an MFI-type framework structure which may be comprised in the zeolitic material obtained according to the inventive process, nor with respect to the number or different types thereof, such that the zeolitic material may by way of example comprise one or more zeolites having an MFI-type framework structure selected from the group consisting of ZSM-5, ZBM-10, [As—Si—O]-MFI, [Fe—Si—O]-MFI, [Ga—Si—O]-MFI, AMS-1B, AZ-1, Bor-C, Boralite C, Encilite, FZ-1, LZ-105, monoclinic H-ZSM-5, Mutinaite, NU-4, NU-5, Silicalite, TS-1, TSZ, TSZ-III, TZ-01, USC-4, USI-108, ZBH, ZKQ-1B, ZMQ-TB, and mixtures of two or more thereof. Specifically, however, the zeolitic material obtained according to the inventive process comprises ZSM-5 and/or ZBM-10 as the one or more zeolites having an MFI-type framework specifically contained therein. As regards the zeolitic material ZBM-10 and in particular its production, reference is made herewith to the disclosure of EP 0 007 081A1 and of EP 0 034 727 A2, respectively. Accordingly to particularly specific embodiments of the inventive process, the zeolitic material obtained comprises ZSM-5 as the specific zeolite having an MFI-type framework structure.

In addition to relating to a process for the production of a zeolitic material having an MFI, MEL, and/or MWW-type framework structure, the present invention also relates to a zeolitic material having an MFI, MEL, and/or MWW-type framework structure which is either obtained by the process according to the present invention or by any conceivable process which leads to a zeolitic material having an MFI, MEL, and/or MWW-type framework structure as obtainable according to the inventive process, wherein in particular the inventive process designates any of the particular and specific embodiments thereof as defined in the present application.

Furthermore, the present invention also relates to a zeolitic material having an MFI, MEL, and/or MWW-type framework structure comprising $YO_2$ and $X_2O_3$ as such, wherein Y is a tetravalent element, and X is a trivalent element, wherein the zeolitic material contains 3 wt.-% or less of one or more elements M based on 100 wt-% of $YO_2$, wherein M stands for sodium, wherein the zeolitic material further comprises one or more elements selected from the group of alkaline earth metals, and wherein 95% by weight or more of the primary particles have a diameter of less than or equal to 1 μm.

According to the present invention, the inventive zeolitic material having an MFI, MEL, and/or MWW-type framework structure as defined according to the particular and specific embodiments thereof in the present application is obtained by the process according to the present invention or by any conceivable process leading to said zeolitic material according to the present invention and, in particular, particular and specific embodiments thereof as defined herein.

According to the present invention, the zeolitic material having an MFI, MEL, and/or MWW-type framework structure comprises $YO_2$. In principle, Y stands for any conceivable tetravalent element, Y standing for either one or several tetravalent elements. Specific tetravalent elements according to the present invention include Si, Sn, Ti, Zr, Ge, and mixtures of two or more thereof. According to the present invention, however, Y comprises Si, wherein more specifically Y is Si.

As regards $X_2O_3$ comprised in the zeolitic material having an MFI, MEL, and/or MWW-type framework structure according to the present invention, X may in principle stand for any conceivable trivalent element, wherein X stands for one or more several trivalent elements. Specific trivalent elements according to the present invention include Al, B, In, Ga, and mixtures of two or more thereof. More specifically, X stands for Al, B, Ga, or mixtures of any two or more of said trivalent elements, wherein more specifically X comprises Al and/or Ga. According to particularly specific embodiments of the present invention, X comprises Al, wherein more specifically X stands for Al.

According to a specific embodiment of the present invention, 96% by weight or more, more specifically 97% by weight or more, more specifically 98% by weight or more, in particular 99% by weight or more of the primary particles of the zeolitic material have a diameter of less than or equal to 1 μm.

Regarding the primary particles of the present invention, there is no particular restriction as to their crystal habit, wherein according to the present invention it is specific that at least a portion of the primary particles are spherical.

The term "spherical" as used in the context of the present invention denotes primary particles which, on investigation by scanning electron microscopy (SEM) at a magnification of from $0.5 \times 10^4$ to $2.0 \times 10^4$, and specifically of from $2.0 \times 10^4$ to $75 \times 10^4$ are substantially free of sharp edges. Accordingly, the term "spherical" denotes, for example, purely spherical or deformed spherical, for example elliptical or cuboid primary particles, wherein the edges are rounded and not sharp in the case of the cuboid primary particles in the abovementioned investigation method in said resolution range.

According to the specific embodiments of the present invention wherein at least a portion of the primary particles are spherical, it is specific that 50% or more of the primary particles are spherical, more specifically 60% or more, more specifically 70% or more, more specifically 80% or more, more specifically 85% or more, and more specifically 90% or more. According to yet further specific embodiments of the present invention, 91% or more of the primary particles, more specifically 92% or more, more specifically 93% or more, more specifically 94% or more, more specifically 95% or more, more specifically 96% or more, and more specifically 97% of the primary particles of the zeolitic material are spherical.

Regarding the primary particles of the zeolitic material, diameters of less than 1 μm are specific for 95% by weight or more thereof, wherein according to specific embodiments wherein at least a portion of the primary particles are spherical, 95% by weight or more of the spherical primary particles have a diameter of less than or equal to 1 μm. More specific are diameters of 900 nm or less, more specifically 800 nm or less, more specifically 700 nm or less, more specifically 600 nm or less, and more specifically 500 nm or less. More specifically, the primary particles of the zeolitic material have a diameter in the range of 5 nm or more, more specifically 10 nm or more, more specifically 20 nm or more, more specifically 30 nm or more, particularly specifically 50 nm or more. The diameters are particularly specifically in the range of from 5 to 800 nm, specifically from 10 to 500 nm, more specifically from 20 to 400 nm, more specifically from 30 to 300 nm, more specifically from 40 to 250 nm, and more specifically from 50 to 200 nm.

Therefore, embodiments of the present invention are specific, wherein 95% by weight or more of the primary particles have a diameter of from 5 to 800 nm, specifically from 10 to 500 nm, more specifically from 20 to 400 nm, more specifically from 30 to 300 nm, more specifically from 40 to 250 nm, and more specifically from 50 to 200 nm.

Furthermore, embodiments of the present invention are specific, wherein 90% or more of the primary particles are spherical, and wherein specifically 95% by weight or more of the spherical primary particles have a diameter of less than or equal to 1 μm, and more specifically of from 5 to 800 nm, more specifically from 10 to 500 nm, more specifically from 20 to 400 nm, more specifically from 30 to 300 nm, more specifically from 40 to 250 nm, and more specifically from 50 to 200 nm.

The diameters of the primary particles as described in the context of the present invention may be determined, for example, via the electron microscopic methods SEM (scanning electron microscopy) and TEM (transmission electron microscopy). The diameters described in the context of the present invention were determined by SEM.

According to the present invention, the zeolitic material having an MFI, MEL, and/or MWW-type framework structure contains 3 wt.-% or less of one or more elements M based on 100 wt.-% of $YO_2$. As regards the one or more elements M, M stands for sodium. According to specific embodiments of the present invention, the zeolitic material contains 3 wt.-% or less of both sodium and potassium based on 100 wt.-% of $YO_2$. As regards the amount of the one or more elements M calculated by weight according to the present invention, said amount refers to the weight of said one or more elements calculated as the element as opposed to being calculated as the oxide or the like. According to the invention, it is further specific that the one or more elements M, of which the zeolitic material contains 3 wt.-% or less, stands for the group of alkaline metals and in particular for Li, Na, K, Rb, and Cs. According to yet further specific embodiments, M stands for the group of both alkali and alkaline earth metals, wherein the alkaline earth metals wherein said alkaline earth metals refer in particular to the elements Mg, Ca, Sr, and Ba, wherein according to said particularly specific embodiments of the present invention wherein the zeolitic material contains 3 wt.-% or less of one or more elements M including alkaline earth metals, said one or more alkaline earth metals M do not include the one or more elements further comprised in the zeolitic material according to any of the particular and specific embodiments of the present invention. More specifically, by way of example, as regards particularly specific embodiments of the present invention wherein the zeolitic material having an MFI, MEL, and/or MWW-type framework structure further comprises Mg as the one or more element selected from the group of alkaline earth metals, the zeolitic material contains 3 wt.-% or less of alkali and alkaline earth metals M, wherein M does not include Mg.

According to the present invention, it is specific that the zeolitic material having an MFI, MEL, and/or MWW-type framework structure contains 1 wt.-% or less of the one or more elements M based on 100 wt.-% of $YO_2$, wherein specifically the zeolitic material contains 0.5 wt.-% or less thereof, more specifically 0.1 wt.-% or less, more specifically 0.05 wt.-% or less, more specifically 0.02 wt.-% or less, more specifically 0.01 wt.-% or less, more specifically 0.005 wt.-% or less, more specifically 0.001 wt.-% or less, more specifically 0.0005 wt.-% or less and more specifically 0.0003 wt.-% or less thereof. According to particularly specific embodiments of the present invention, the zeolitic material is substantially free of the one or more elements M, wherein at most traces of said one or more elements M are contained therein, said traces constituting less than 0.0001 wt.-% based on 100 wt.-% of $YO_2$ comprised in the zeolitic material.

As regards the one or more elements selected from the group of alkaline earth metals further comprised in the zeolitic material in addition to the framework elements $YO_2$ and $X_2O_3$, said one or more alkaline earth metals may stand for any alkaline earth metal or a combination of two or more alkaline earth metals, wherein specifically the one or more element selected from the group of alkaline earth metals is selected from the group consisting of Mg, Ca, Ba, Sr, and mixtures of two or more thereof, wherein more specifically the one or more elements comprise Mg and/or Ca. According to particularly specific embodiments, the one or more elements selected from the group of alkaline earth metals comprise Mg, wherein more specifically Mg is further comprised in the zeolitic material as the one or more elements selected from the group of alkaline earth metals.

Regarding the amount in which the one or more element selected from the group of alkaline earth metals may be contained in the zeolitic material having an MFI, MEL, and/or MWW-type framework structure, no particular restriction applies in this respect according to the present invention, such that in principle any conceivable amount thereof may be comprised therein. Thus, by way of example, the one or more element selected from the group of alkaline earth metals further comprised in the zeolitic material may be contained therein in an amount ranging anywhere from 0.1 to 15 wt.-% based on the total weight of the zeolitic material, wherein specifically the one or more elements are further comprised therein in an amount ranging from 0.5 to 10 wt.-%, more specifically from 1 to 7 wt.-%, more specifically from 2 to 5 wt.-%, more specifically from 3 to 4.5 wt.-%, and more specifically from 3.5 to 4.3 wt.-%. According to particularly specific embodiments of the present invention, the one or more element selected from the group of alkaline earth metals further comprised in the zeolitic material or contained therein in an amount ranging from 3.8 to 4.1 wt.-%. As regards the one or more alkaline earth metals further comprised in the zeolitic material, there is no particular restriction as to the manner in which said one or more element is contained in the zeolitic material. Thus, by way of example, said one or more alkaline earth metal elements may be comprised on the outer surface of the particles of the zeolitic material and/or within the porous structure of said materials, wherein it is specific that at least a portion of said one or more alkaline earth metal elements is contained in the porous structure of the zeolitic material, in particular as non-framework elements of the zeolitic material which do not constitute the one or more framework structures of the zeolitic material and are accordingly present in the pores and/or cavities formed by the respective framework structure and typical for zeolitic materials in general.

As regards the respective amounts of $YO_2$ and $X_2O_3$ comprised in the zeolitic material having an MFI, MEL, and/or MWW-type framework structure, there is no particular restriction as to the amounts in which they may be respectively contained therein, nor with respect to the molar ratio of $YO_2$ to $X_2O_3$ displayed by the zeolitic material. Thus, by way of example, the zeolitic material may display a $YO_2:X_2O_3$ atomic ratio ranging anywhere from 10 to 1500, wherein specifically the atomic ratio ranges from 30 to 1200, more specifically from 50 to 900, more specifically from 70 to 700, more specifically from 80 to 500, and even more specifically from 90 to 300. According to particularly specific embodiments of the present invention, the zeolitic material having an MFI, MEL, and/or MWW-type framework structure displays a $YO_2:X_2O_3$ atomic ratio in the range of from 100 to 250.

As concerns the specific zeolitic material having an MFI, MEL, and/or MWW-type framework structure of the present invention, there is no particular restriction as to the specific MFI and/or MEL and/or MWW-type material, such that any conceivable one or more zeolites having an MFI and/or MEL and/or MWW-type framework structure may be contained therein. Thus, by way of example, according to embodiments of the present invention wherein the zeolitic material comprises one or more zeolites having an MWW-type framework structure, said one or more zeolites having an MWW-type framework structure may include one or more zeolites selected from the group consisting of MCM-22, [Ga—Si—O]-MWW, [Ti—Si—O]-MWW, ERB-1, ITQ-1, PSH-3, SSZ-25, and mixtures of two or more thereof. It is, however, specific according to embodiments of the present invention wherein the zeolitic material comprises one or more zeolites having an MWW-type framework structure which may be employed for the conversion of oxygenates to olefins, wherein more specifically the zeolitic material according to said particularly specific embodiments comprises MCM-22 and/or MCM-36.

Same applies accordingly with respect to the one or more zeolites having an MEL-type framework structure which may be comprised in the zeolitic material of the present invention. Thus again, by mere way of example, the one or more zeolites having an MEL-type framework structure which may be comprised in the zeolitic material may include one or more zeolites selected from the group consisting of ZSM-11, [Si—B—O]-MEL, Bor-D (MFI/MEL-intergrowth), Boralite D, SSZ-46, Silicalite 2, TS-2, and mixtures of two or more thereof. In this case also, it is specific that the one or more zeolites having an MEL-type framework structure may be employed for the conversion of oxygenates to olefins, wherein according to a particularly specific embodiment thereof, the zeolitic material comprises ZSM-11.

As mentioned above, however, the zeolitic material of the present invention comprises one or more zeolites having an MFI-type framework structure, and in particular one or more zeolites of the MFI-type framework structure which may be employed in the conversion of oxygenates to olefins. According to said specific embodiments of the zeolitic material, no particular restriction applies with respect to the type of the one or more zeolites having an MFI-type framework structure which may be comprised therein, such that the zeolitic material may by way of example comprise one or more zeolites selected from the group consisting of ZSM-5, ZBM-10, [As—Si—O]-MFI, [Fe—Si—O]-MFI, [Ga—Si—O]-MFI, AMS-1B, AZ-1, Bor-C, Boralite C, Encilite, FZ-1, LZ-105, monoclinic H-ZSM-5, Mutinaite, NU-4, NU-5, Silicalite, TS-1, TSZ, TSZ-III, TZ-01, USC-4, USI-108, ZBH, ZKQ-1B, ZMQ-TB, and mixtures of two or more thereof. Specifically, however, the zeolitic material comprises ZSM-5 and/or ZBM-10 as the one or more zeolites having an MFI-type framework. Accordingly to particularly specific embodiments of the inventive process, the zeolitic material comprises ZSM-5.

Furthermore, there is no particular restriction according to the present invention as to the suitable physical and/or chemical characteristics of the inventive zeolitic materials. Thus, as regards, for example, the porosity and/or surface area of the inventive materials, these may adopt any conceivable values. In particular, as regards the BET surface area of the zeolitic materials as determined according to DIN 66131, it may accordingly range anywhere from 200 to 900 $m^2/g$, wherein specifically the BET surface area ranges from 250 to 700 $m^2/g$, more specifically from 300 to 600 $m^2/g$, more specifically from 350 to 550 $m^2/g$, more specifically from 380 to 500 $m^2/g$, more specifically from 400 to 470 $m^2/g$, and more specifically from 420 to 450 $m^2/g$. According to particularly specific embodiments of the present invention, the BET surface area of the zeolitic material as determined according to DIN 66131 ranges from 425 to 440 $m^2/g$.

According to the present invention, it is further specific that the zeolitic material displays a low water uptake, i.e. a high hydrophobicity, wherein by way of example the water uptake of the zeolitic material may be 10.0 wt.-% or less.

Specifically, however, the inventive zeolitic material displays a water uptake of 10.0 wt.-% or less, more specifically of 7.4 wt.-% or less, more specifically of 6.2 wt.-% or less, more specifically of 6.0 wt.-% or less, more specifically of 5.0 wt.-% or less, more specifically of 4.5 wt.-% or less, more specifically of 4.2 wt.-% or less, more specifically of 3 wt.-% or less, and more specifically of 2.2 wt.-% or less. According to the invention the zeolitic material displays a water uptake of 2 wt.-% or less, and even more specifically of 1.5 wt.-% or less.

Depending on the specific needs of its application, the zeolitic materials of the present invention can be employed as such, like in the form of a powder, a spray powder or a spray granulate obtained from above-described separation techniques, e.g. decantation, filtration, centrifugation, or spraying.

In many industrial applications, it is often desired on the part of the user not to employ the zeolitic material as powder or sprayed material, i.e. the zeolitic material obtained by the separation of the material from its mother liquor, optionally including washing and drying, and subsequent calcination, but a zeolitic material which is further processed to give moldings.

Such moldings are required particularly in many industrial processes, e.g. in many processes wherein the zeolitic material of the present invention is employed as catalyst or adsorbent.

Accordingly, the present invention also relates to a molding comprising the inventive zeolitic material according to any of the particular and specific embodiments thereof as defined in the present application. The present invention accordingly also relates to a molding containing a zeolitic material as described above.

In general, the molding may comprise any conceivable compounds in addition to the zeolitic material according to the present invention, provided that it is ensured that the resulting molding is suitable for the desired application.

In the context of the present invention, it is specific to use at least one suitable binder material in the production of the molding. In this specific embodiment, it is more specific to prepare a mixture of zeolitic material and the at least one binder material.

Accordingly, the present invention also describes a process for the production of a molding, containing a zeolitic material as described above, comprising the step of
(A) preparation of a mixture containing a zeolitic material as described above, or a zeolitic material obtainable by a process as described above, and at least one binder material.

Suitable binder materials are in general all compounds which impart adhesion and/or cohesion between the particles of the zeolitic material which are to be bound, which adhesion and cohesion are over and above the physisorption which may be present without a binder material. Examples of such binder materials are metal oxides, such as $SiO_2$, $Al_2O_3$, $TiO_2$, $ZrO_2$ or MgO or clays or mixtures of two or more of these compounds.

As $Al_2O_3$ binder materials, clay minerals and naturally occurring or synthetic aluminas, for example alpha-, beta-, gamma-, delta-, eta-, kappa-, chi-or theta-alumina and the inorganic or organometallic precursor compounds thereof, for example gibbsite, bayerite, boehmite, pseudoboehmite or trialkoxyaluminates, for example aluminum triisopropylate, are in particular suitable. Further specific binder materials are amphiphilic compounds having a polar and a nonpolar moiety, and graphite. Further binder materials are, for example, clays, such as montmorillonites, kaolins, bentonites, halloysites, dickites, nacrites or anaxites.

These binder materials may be used as such. It is also possible in the context of the present invention to use compounds from which the binder is formed in at least one further step in the production of the moldings. Examples of such binder material precursors are tetraalkoxysilanes, tetraalkoxytitanates, tetraalkoxyzirconates or a mixture of two or more different tetraalkoxysilanes or a mixture of two or more different tetraalkoxytitanates or a mixture of two or more different tetraalkoxyzirconates or a mixture of at least one tetraalkoxysilane and at least one tetraalkoxytitanate or of at least one tetraalkoxysilane and at least one tetraalkoxyzirconate or of at least one tetraalkoxytitanate and at least one tetraalkoxyzirconate or a mixture of at least one tetraalkoxysilane and at least one tetraalkoxytitanate and at least one tetraalkoxyzirconate.

In the context of the present invention, binder materials which either completely or partly comprise $SiO_2$ or are a precursor of $SiO_2$ from which $SiO_2$ is formed in at least one further step in the production of the moldings are very particularly specific. In this context, both colloidal silica and wet process silica and dry process silica can be used. These are very particularly specifically amorphous silica, wherein the size of the silica particles is in the range of from 5 to 100 nm and the surface area of the silica particles is in the range of from 50 to 500 $m^2/g$.

Colloidal silica, specifically as an alkaline and/or ammoniacal solution, more specifically as an ammoniacal solution, is commercially available, inter alia, as Ludox®, Syton®, Nalco® or Snowtex®. Wet process silica is commercially available, inter alia, as Hi-Sil®, Ultrasil®, Vulcasil®, Santocel®, Valron-Estersil®, Tokusil® or Nipsil®. Dry process silica is commercially available, inter alia, as Aerosil®, Reolosil®, Cab-O-Sil®, Fransil® or ArcSilica®. Inter alia, an ammoniacal solution of colloidal silica is specific in the context of the present invention.

Accordingly, the present invention also relates to a molding as described above, additionally containing $SiO_2$ as binder material.

The present invention also relates to a process as described above, wherein the binder material employed according to (A) is $SiO_2$-containing or -forming binder material. Accordingly, the present invention also relates to a process as described above, wherein the binder material is a colloidal silica.

The binder materials are specifically used in an amount which leads to the finally resulting moldings, whose binder content is up to 80, more specifically from 5 to 80, more specifically from 10 to 70, more specifically from 10 to 60, more specifically from 15 to 50, more specifically from 15 to 45, particularly specifically from 15 to 40, % by weight, based in each case on the total weight of the finally resulting molding.

The mixture of binder material or precursor for a binder material and the zeolitic material can be mixed with at least one further compound for further processing and for forming a plastic mass. Inter alia, pore formers are specific here. Pore formers which may be used in the process according to the present invention are all compounds which, with regard to the prepared molding, provide a certain pore size, a certain pore size distribution and/or a certain pore volume.

Specifically used pore formers in the process according to the present invention are polymers which are dispersible, suspendable or emulsifiable in water or in aqueous solvent mixtures. Specific polymers here are polymeric vinyl compounds, for example polyalkylene oxides, such as polyethylene oxides, polystyrene, polyacrylates, polymethacrylates, polyolefins, polyamides and polyesters, carbohydrates, such as cellulose or cellulose derivatives, for example methylcellulose, or sugar or natural fibers. Further suitable pore formers are, for example, pulp or graphite.

If pore formers are used in the preparation of the mixture according to (A), the polymer content of the mixture according to (A) is specifically in the range of from 5 to 90, more specifically from 15 to 75, particularly specifically from 25 to 55, % by weight, based in each case on the amount of zeolitic material in the mixture according to (A). If it is desirable for the pore size distribution to be achieved, a mixture of two or more pore formers may also be used.

In a particularly specific embodiment of the process according to the present invention, as described below, the pore formers are removed in a step (E) by calcination to give the porous molding. According to a specific embodiment of the process according to the present invention, moldings which have pores in the range of at least 0.6, specifically from 0.6 to 0.8, particularly specifically from more than 0.6 to 0.8, ml/g, determined according to DIN 66134, are obtained.

The specific surface area of the molding according to the present invention, determined according to DIN 66131, is in general at least 250 m$^2$/g, specifically at least 290 m$^2$/g, particularly specifically at least 300 m$^2$/g. For example, the specific surface area may be from 250 to 400 m$^2$/g or from 290 to 450 m$^2$/g or from 300 to 500 m$^2$/g.

Accordingly, the present invention also relates to a molding as described above, having a specific surface area of at least 250 m$^2$/g, containing pores having a pore volume of at least 0.6 ml/g.

In the preparation of the mixture according to (A), at least one pasting agent is added in a likewise specific embodiment of the process according to the present invention. Pasting agents which may be used are all compounds suitable for this purpose. These are specifically organic, in particular hydrophilic, polymers, for example cellulose, cellulose derivatives, such as methylcellulose, starch, such as potato starch, wallpaper paste, polyacrylates, polymethacrylates, polyvinyl alcohol, polyvinylpyrrolidone, polyisobutene, polyethyleneglycol or polytetrahydrofuran. In particular, compounds which also act as pore formers can accordingly be used as pasting agents. In a particularly specific embodiment of the process according to the present invention, as described below, these pasting agents are removed in a step (E) by calcination to give the porous molding.

According to a further embodiment of the present invention, at least one acidic additive is introduced during the preparation of the mixture according to (A). Organic acidic compounds can be removed by calcination in the specific step (E), as described below, are very particularly specific. Carboxylic acids, for example formic acid, oxalic acid and/or citric acid, are particularly specific. It is also possible to use two or more of these acidic compounds.

The order of addition of the components of the mixture according to (A) which contains the zeolitic material is not critical. It is possible both first to add the at least one binder material, subsequently the at least one pore former, the at least one acidic compound and finally the at least one pasting agent and it is possible to interchange the sequence with regard to the at least one binder material, the at least one pore former, the at least one acidic compound and the at least one pasting agent.

After the addition of the binder material to the zeolite-containing solid, to which optionally at least one of the compounds described above had already been added, the mixture according to (A) is as a rule homogenized for from 10 to 180 min. Inter alia, kneaders, edge mills or extruders are particularly specifically used for the homogenization. The mixture is specifically kneaded. On an industrial scale, treatment in an edge mill is specific for homogenization.

Accordingly, the present invention also describes a process as described above, comprising the steps
(A) preparation of a mixture containing a zeolitic material as described above, or a zeolitic material obtainable by a process as described above, and at least one binder material;
(B) kneading of the mixture.

In the homogenization, as a rule temperatures of from about 10° C. to the boiling point of the pasting agent and atmospheric or slightly superatmospheric pressure are employed. Subsequently at least one of the compounds described above can be optionally added. The mixture thus obtained is homogenized, specifically kneaded, until an extrudable plastic mass has formed. The homogenized mixture is molded according to a more specific embodiment of the present invention.

In the context of the present invention, specific shaping methods are those in which the molding is effected by extrusion in conventional extruders, for example to give extrudates having a diameter of, specifically, from 1 to 10 mm, particularly specifically from 2 to 5 mm. Such extrusion apparatuses are described, for example, in Ullmann's Enzyklopädie der Technischen Chemie, 4th Edition, Vol. 2, page 295 et seq., 1972. In addition to the use of an extruder, a ram extruder may likewise specifically be used for the molding.

In principle, however, all known and/or suitable kneading and molding apparatuses and methods can be used for the shaping. Examples of these include:
(a) bricketting, i.e. mechanical pressing with or without addition of additional binder material;
(b) pelleting, i.e. compacting by circular and/or rotational movements;
(c) sintering, i.e. the material to be molded is subjected to a thermal treatment.

For example, the shaping can be selected from the following group, wherein the combination of at least two of these methods is explicitly included: bricketting by means of a ram press, roll press, ring-roll press, bricketting without binder; pelleting, melting, spinning techniques, deposition, foaming, spray-drying; combustion in a shaft furnace, convection furnace, travelling grate, rotary kiln, edge mill.

The compacting may take place at ambient pressure or at superatmospheric pressure, for example at from 1 to several hundred bar. Furthermore, the compacting may take place at ambient temperature or at a temperature higher than the ambient temperature, for example at from 20 to 300° C. If drying and/or combustion are part of the shaping step, temperatures of up to 1,500° C. are conceivable. Finally, the compacting may take place in the ambient atmosphere or in a controlled atmosphere. Controlled atmospheres are, for example, inert gas atmospheres or reducing and/or oxidizing atmospheres.

Accordingly, the present invention also describes a process for the production of a molding as described above, comprising the steps
(A) preparation of a mixture containing a zeolitic material as described above, or a zeolitic material obtainable by a process as described above, and at least one binder material;
(B) kneading of the mixture;
(C) molding of the kneaded mixture to give at least one molding.

The shape of the moldings produced according to the invention can be chosen as desired. In particular, inter alia spheres, oval shapes, cylinders or tablets are possible.

In the context of the present invention, the molding is particularly specifically carried out by extrusion of the kneaded mixture obtained according to (B), more specifically substantially cylindrical extrudates having a diameter in the range of from 1 to 20 mm, specifically from 1 to 10 mm, more specifically from 2 to 10 mm, and particularly specifically from 2 to 5 mm, being obtained as extrudates.

In the context of the present invention, step (C) is specifically followed by at least one drying step. This at least one drying step is effected at temperatures in general in the range of from 80 to 160° C., specifically from 90 to 145° C., particularly specifically from 100 to 130° C., wherein the duration of drying generally is 6 hours or more, for example in the range of from 6 to 24 hours. However, depending on the moisture content of the material to be dried, shorter drying times, for example about 1, 2, 3, 4 or 5 hours, are also possible.

Before and/or after the drying step, the specifically obtained extrudate can, for example, be milled. Specifically, granules or chips having a particle diameter of from 0.1 to 5 mm, in particular from 0.5 to 2 mm, are obtained.

Accordingly, the present invention also describes a process for the production of a molding as described above, comprising the steps
  (A) preparation of a mixture containing a zeolitic material as described above, or a zeolitic material obtainable by a process as described above, and at least one binder material;
  (B) kneading of the mixture;
  (C) molding of the kneaded mixture to give at least one molding;
  (D) drying of the at least one molding.

In the context of the present invention, step (D) is specifically followed by at least one calcination step. The calcination is carried out at a temperature in general in the range of from 350 to 750° C., specifically from 450 to 600° C.

The calcination can be effected under any suitable gas atmosphere, air and/or lean air being specific. Furthermore, the calcination is specifically carried out in a muffle furnace, a rotary kiln and/or a belt calcination furnace, wherein the duration of calcination generally is 1 hour or more, for example in the range of from 1 to 24 or from 3 to 12 h. Accordingly, it is possible in the process according to the present invention, for example, to calcine the moldings once, twice or more often for in each case at least one hour, for example in each case in the range of from 3 to 12 h, wherein the temperatures during the calcination step can remain the same or can be changed continuously or discontinuously. If calcination is effected twice or more often, the calcination temperatures in the individual steps may be different or identical.

Accordingly, the present invention also relates to a process for the production of moldings as described above, comprising the steps
  (A) preparation of a mixture containing a zeolitic material as described above, or a zeolitic material obtainable by a process as described above, and at least one binder material;
  (B) kneading of the mixture;
  (C) molding of the kneaded mixture to give at least one molding;
  (D) drying of the at least one molding;
  (E) calcination of the at least one dried molding.

After the calcination step, the calcined material can, for example, be comminuted. Specifically, granules or chips having a particle diameter of from 0.1 to 5 mm, in particular from 0.5 to 2 mm, are obtained.

Before and/or after the drying and/or before and/or after the calcination, the at least one molding can be treated with a concentrated or dilute Broenstedt acid or with a mixture of two or more Broenstedt acids. Suitable acids are, for example, hydrochloric acid, sulfuric acid, phosphoric acid, nitric acid or carboxylic acids, dicarboxylic acids or oligo-or polycarboxylic acids, such as nitrilotriacetic acid, sulfosalicylic acid or ethylenediaminotetraacetic acid.

Specifically, this at least one treatment with at least one Broenstedt acid is followed by at least one drying step and/or at least one calcination step, which in each case is carried out under the conditions described above.

According to a further specific embodiment of the process according to the present invention, the catalyst extrudates can be subjected to a steam treatment for better hardening, after which once again specifically drying is effected at least once and/or calcination is effected at least once. For example, after at least one drying step and at least one subsequent calcination step, the calcined molding is subjected to steam treatment and then once again dried at least once and/or calcined at least once.

The moldings obtained according to the invention have hardnesses which are in general in the range of from 2 to 40 N, specifically in the range of from 5 to 40 N, particularly specifically from 10 to 40 N.

The present invention accordingly also relates to a molding as described above, having a cutting hardness of from 2 to 40 N.

In the present invention, the hardness described above was determined on an apparatus from Zwick, type BZ2.5/TS1S with a preliminary force of 0.5 N, a feed velocity under the preliminary force of 10 mm/min and a subsequent test velocity of 1.6 mm/min. The apparatus had a fixed turntable and a freely movable punch with built-in blade of 0.3 mm thickness. The movable punch with the blade was connected to a load cell for force pick-up and, during the measurement, moved toward the fixed turntable on which the catalyst molding to be investigated was present. The test apparatus was controlled by means of a computer which registered and evaluated the measured results. The value obtained is the mean value of the measurements for 10 catalyst moldings in each case. The catalyst moldings had a cylindrical geometry, wherein their average length corresponds to about twice to three times the diameter, and were loaded with the blade of 0.3 mm thickness with increasing force until the molding had been cut through. The blade was applied to the molding perpendicularly to the longitudinal axis of the molding. The force required for this purpose is the cutting hardness (unit N).

The present invention accordingly also relates to a molding, obtainable by a process according any one of the above mentioned embodiments.

The at least one molding according to the invention and/or the molding produced according to the invention can generally be used in all processes or operations in which the properties of the molding and in particular of the zeolitic material according to the present invention contained in the molding or a zeolitic material prepared according to the invention are desired. Very particularly specifically, the at least one molding according to the invention or the molding produced according to the invention is used as a catalyst in chemical reactions.

The present invention accordingly relates to the use of a molding as described above, or of a molding obtainable by a process as described above, as catalyst.

In general, the zeolitic material having an MFI, MEL, and/or MWW-type framework structure as described in the present application and in particular according to the particular and specific embodiments described herein can be used in any suitable application, wherein said zeolitic material is specifically used as a molecular sieve, catalyst, catalyst support, and/or as an absorbent. For example, the inventive zeolitic material can be used as molecular sieve to dry gases or liquids, for selective molecular separation, e.g. for the separation of hydrocarbons or amines; as ion exchanger; as chemical carrier; as adsorbent, in particular as adsorbent for the separation of hydrocarbons or amines; or as a catalyst. Most specifically, the zeolitic material according to the present invention is used as a catalyst and/or as a catalyst support.

According to a specific embodiment of the present invention, the zeolitic material is used in a catalytic process, specifically as a catalyst and/or catalyst support, and more specifically as a catalyst. In general, the zeolitic material of the invention can be used in any conceivable catalytic process, wherein processes involving the conversion of at least one organic compound are specific, more specifically of organic compounds comprising at least one carbon-carbon and/or carbon-oxygen and/or carbon-nitrogen bond, more specifically of organic compounds comprising at least one carbon-carbon and/or carbon-oxygen bond, and even more specifically of organic compounds comprising at least one carbon-oxygen bond.

Thus, according to a particularly specific embodiment of the present invention, the inventive zeolitic material is used as a catalyst in the conversion of oxygenates to olefins, in a methanol to gasoline (MTG) process, in a biomass to olefins and/or biomass to aromatics process, in a methane to benzene process, in a process for the alkylation of aromatics, or in a fluid catalytic cracking (FCC) process. According to the invention, the zeolitic material is employed in a process for the conversion of oxygenates to olefins, wherein more specifically the zeolitic material is used as a catalyst in a dimethylether to olefin process (DTO), methanol to olefin (MTO) process, in a methanol to propylene (MTP) process, and/or in a methanol to propylene/butylene (MT3/4) process.

In addition to relating to a zeolitic material having an MFI, MEL, and/or MWW-type framework structure and to a process for the production of such a zeolitic material, the present invention further relates to a process for the conversion of oxygenates to olefins. In particular, the present invention further concerns a process for the conversion of oxygenates to olefins comprising (I) providing a gas stream comprising one or more oxygenates,
(II) contacting the gas stream with a catalyst comprising a zeolitic material according to the present invention and in particular according to any of the particular and specific embodiments thereof.

As regards the catalyst which is used in the inventive process, no particular restriction applies in its respect provided that it comprises a zeolitic material according to the present invention and that it is suited for the conversion of at least one oxygenate to at least one olefin. Again, this applies in particular relative to the particular and specific embodiments according to the present invention as defined in the present application. According to particularly specific embodiments of the inventive process for the conversion of oxygenates to olefins, however, the catalyst comprises a molding according to any of the particular and specific embodiments of the present invention, wherein the molding accordingly comprises a zeolitic material according to any of the particular and specific embodiments of the present invention.

Concerning the gas stream according to step (I), no particular restriction applies according to the present invention relative to the one or more oxygenates which may be contained therein, provided that said one or more oxygenates may be converted to at least one olefin upon contacting thereof with the catalyst comprising a zeolitic material according to the present invention and in particular according to any of the particular and specific embodiments thereof as defined herein. According to the present invention, it is, however, specific that the one or more oxygenates contained in the gas stream provided in step (I) comprise one or more oxygenates selected from the group consisting of aliphatic alcohols, ethers, carbonyl compounds, and mixtures of two or more thereof. According to the inventive process for the conversion of oxygenates to olefins, it is further specific that the one or more oxygenates comprised in the gas stream is selected from the group consisting of $C_1$-$C_6$-alcohols, di-$C_1$-$C_3$-alkyl ethers, $C_1$-$C_6$-aldehydes, $C_2$-$C_6$-ketones, and mixtures of two or more thereof, more specifically from the group consisting of $C_1$-$C_4$-alcohols, di-$C_1$-$C_2$-alkyl ethers, $C_1$-$C_4$-aldehydes, $C_2$-$C_4$-ketones, and mixtures of two or more thereof. According to yet further specific embodiments of the inventive process, the gas stream provided in step (I) comprises one or more oxygenates selected from the group consisting of methanol, ethanol, n-propanol, isopropanol, butanol, dimethyl ether, diethyl ether, ethyl methyl ether, diisopropyl ether, di-n-propyl ether, formaldehyde, dimethyl ketone, and mixtures of two or more thereof, wherein it is yet further specific that the one or more oxygenates comprised in the gas stream according to (I) is selected from the group consisting of methanol, ethanol, n-propanol, isopropanol, butanol, dimethyl ether, diethyl, ethyl methyl ether, diisopropyl ether, di-n-propyl ether, formaldehyde, dimethyl ketone, and mixtures of two or more thereof, and more specifically from the group consisting of methanol, ethanol, dimethyl ether, diethyl ether, ethyl methyl ether, and mixtures of two or more thereof. According to particularly specific embodiments of the inventive process for the conversion of oxygenates to olefins, the gas stream provided in step (I) comprises methanol and/or dimethyl ether, wherein dimethyl ether is comprised as the one or more oxygenates in the gas stream according to (I).

Regarding the content of oxygenates in the gas stream according to (I) in the inventive process for the conversion of oxygenates to olefins, no particular restriction applies provided that the contacting of the gas stream according to (II) with the catalyst comprising a zeolitic material according to the present invention allows for the conversion of at least one oxygenate to at least one olefin. According to a specific embodiment of the inventive process, the content of oxygenates in the gas stream according to (I) lies in the range of from 30 to 100 vol.-% based on the total volume of the gas stream, wherein the content refers in particular to a gas stream at a temperature in the range of from 200 to 700° C. and at a pressure of 101.3 kPa, specifically at a temperature in the range of from 250 to 650° C., more specifically at a temperature of from 300 to 600° C., more specifically at a temperature of 350 to 560° C., more specifically at a temperature in the range of from 400 to 540° C., more specifically at a temperature in the range of from 430 to 520° C., and more specifically at a temperature in the range of from 450 to 500° C. at a pressure of 101.3 kPa. According to the present invention, it is further specific that the content of oxygenates in the gas stream according to (I) is comprised in the range of from 30 to 99.9 vol.-% based on the total volume of the gas stream, and more specifically in the range of from 30 to 99 vol.-%, more specifically from 30 to 95 vol.-%, more specifically from 30 to 90 vol.-%, more specifically from 30 to 80 vol.-%, more specifically from 30 to 70 vol.-%, more specifically from 30 to 60 vol.-%, and more specifically from 30 to 50 vol.-%. According to a particularly specific embodiment of the inventive process, the content of the one or more oxygenates in the gas stream according to (I) lies in the range of from 30 to 45 vol.-%.

Therefore, embodiments of the inventive process for the conversion of oxygenates to olefins are specific, wherein the gas stream provided in step (I) contains from 30 to 100 vol.-% of oxygenates based on the total volume of the gas stream.

Regarding the further components which may be contained in the gas stream according to (I) of the inventive process, in principle there is no restriction neither with respect to the number nor with respect to the amount of said one or more further components to the one or more oxygenates, provided that when bringing said gas stream into contact with a zeolitic material according to the present invention in step (II), at least one of the one or more oxygenates may be converted to at least one olefin. Accordingly, one or more inert gases may for example be contained in the gas stream according to (I) in addition to the one or more oxygenates such as for example one or more noble gases, nitrogen gas, carbon monoxide, carbon dioxide, water, and mixtures of two or more thereof. Alternatively, or in addition to these, the one or more inert gases may comprise unwanted side-products which are recycled such as paraffins, olefinic products with 5 or more carbon atoms, aromatics, or mixtures of two or more thereof, which are produced according to any of the particular and specific embodiments of the inventive process for the conversion of oxygenates to olefins. According to particularly specific embodiments of the present invention, the gas stream according to (I) of the inventive process further comprises water in addition to the one or more oxygenates.

According to the particularly specific embodiments of the inventive process, wherein water is contained in the gas stream according to (I) in addition to the one or more oxygenates, no restriction applies in principle relative to the amount of water which may be contained in the gas stream, provided that at least one of the oxygenates may be converted in step (II) to at least one olefin upon contacting of the gas stream with a catalyst according to the present invention. Thus, by way of example, the gas stream provided in step (I) may contain 60 vol.-% water or less based on the total volume of the gas stream, wherein according to particular embodiments which are specific the water content in the gas stream ranges from 5 to 60 vol.-% based on the total volume of the gas stream, wherein it is specific that the water content ranges from 10 to 55 vol. %, and more specifically from 20 to 50 vol.-%. According to particularly specific embodiments of the present invention, water is contained in the gas stream according to (I) in an amount of 30 to 45 vol.-% in addition to the one or more oxygenates.

According to alternatively specific embodiments, however, little to no water is contained in the gas stream provided in step (I) and in particular, the water content in the gas stream is 5 vol.-% or less, more specifically 3 vol.-% or less, more specifically 1 vol.-% or less, more specifically 0.5 vol.-% or less, more specifically 0.1 vol.-% or less, more specifically 0.05 vol.-% or less, more specifically 0.01 vol.-% or less, more specifically 0.005 vol.-% or less, and more specifically 0.001 vol.-% or less.

Therefore, in one or more embodiments, the gas stream provided in step (I) contains 60 vol.-% or less of water based on the total volume of the gas stream.

According to a particularly specific embodiment of the inventive process for the conversion of oxygenates to olefins, the gas stream according to (I) originates from a pre-reaction, specifically from the conversion of one or more alcohols to one or more ethers, and in particular from the conversion of one or more alcohols selected from the group consisting of methanol, ethanol, n-propanol, isopropanol, and mixtures of two or more thereof, more specifically from the group consisting of methanol, ethanol, n-propanol, and mixtures of two or more thereof, wherein the gas stream provided in (I) originates from a pre-reaction of methanol and/or ethanol and specifically from methanol which at least in part is converted to one or more di-$C_1$-$C_2$-alkyl ethers, specifically to one or more di-$C_1$-$C_2$-alkyl ethers selected from the group consisting of dimethylether, diethylether, ethylmethylether, and mixtures of two or more thereof. According to a particularly specific embodiment of the inventive process, the gas stream provided in step (I) originates from a pre-reaction, wherein methanol is at least in part converted to dimethylether.

According to the particularly specific embodiments of the present invention, wherein the gas stream provided in step (I) originates from a pre-reaction of one or more alcohols, there is principally no particular restriction relative to the reaction and to the reaction products of the conversion of one or more alcohols, provided that the pre-reaction leads to a gas stream comprising one or more oxygenates which upon contacting with a catalyst according to the invention in step (II) may lead to the conversion of one of the oxygenates to at least one olefin. According to said specific embodiments, it is further specific that the pre-reaction for the conversion of at least one alcohol leads to at least one ether and in particular to at least one dialkyl ether, wherein the pre-reaction is a dehydration reaction, wherein water is produced as a secondary product from the condensation reaction to one or more dialkyl ethers. According to the particular and specific embodiments of the present invention wherein the gas stream provided in step (I) originates from a pre-reaction, it is particularly specific according to the inventive process that a gas stream resulting from such a pre-reaction is directly provided in step (I) of the inventive process without having been subject to any type of workup.

As regards the particular conditions under which the gas stream is contacted with a catalyst according to the present invention in step (II), no particular restriction applies in this respect provided that the conversion of at least one oxygenate to at least one olefin may be realized. This, for example, applies to the temperature at which the contacting in step (II) takes place. Accordingly, said contacting of the gas stream in step (II) may be conducted according to the inventive process at a temperature in the range of from 200 to 700° C., wherein it is specific that the contacting is conducted at a temperature in the range of from 250 to 650° C., more specifically of from 300 to 600° C., more specifically of from 350 to 560° C., more specifically of from 400 to 540° C., and more specifically of from 430 to 520° C. According to a particularly specific embodiment of the inventive process, the contacting of the gas stream in step (II) is conducted at a temperature in the range of from 450 to 500° C.

Accordingly, in one or more embodiments, contacting of the gas stream with the zeolitic material in step (II) is performed at a temperature in the range of 200 to 700° C.

Same applies accordingly relative to the pressure under which the gas stream is contacted with a catalyst according to the present invention in step (II) of the inventive process. Thus, in principle, said contacting may be conducted at any conceivable pressure, provided that at least one oxygenate may be converted to at least one olefin upon contacting of the gas stream with the catalyst. Accordingly, by way of example, the contacting in step (II) may be conducted at a pressure in the range of from 0.1 to 10 bar, wherein the pressure as defined in the present application designates the absolute pressure such that a pressure of 1 bar upon contacting of the gas stream with the catalyst corresponds to the normal pressure of 1.03 kPa. According to the inventive process, contacting in step (II) is specifically performed at a pressure of from 0.3 to 7 bar, more specifically of from 0.5 to 5 bar, more specifically of from 0.7 to 3 bar, more specifically of from 0.8 to 2.5 bar, and more specifically of from 0.9 to 2.2 bar. According to a particularly specific embodiment of the inventive process, contacting of the gas stream in step (II) is conducted at a pressure of from 1 to 2 bar.

Therefore, embodiments of the present invention are specific, wherein contacting of the gas stream with the zeolitic material in step (II) is performed at a pressure in the range of 0.1 to 10 bar.

Furthermore, no particular restriction applies relative to the manner in which the inventive process for the conversion of oxygenates to olefins is conducted, such that both a non-continuous mode as well as a continuous mode may be applied to the inventive process, wherein the non-continuous process may for example be conducted as a batch-process. According to the present invention, it is, however, specific that the inventive process for the conversion of oxygenates to olefins is at least in part performed in a continuous mode.

As regards the specific embodiments of the inventive process, wherein it is at least in part performed in a continuous mode, in principle no restrictions apply relative to the weight hourly space velocity (WHSV) at which the process is conducted, provided that the conversion of at least one oxygenate to at least one olefin may be realized. Accordingly, weight hourly space velocities may be chosen for the contacting in step (II) which lie in the range of from 0.5 to 50 per hour, wherein specifically weight hourly space velocities of from 1 to 30 per hour are chosen, more specifically of from 2 to 20 per hour, more specifically of from 3 to 15 per hour, and more specifically of from 4 to 10 per hour. According to a particularly specific embodiment of the inventive process, wherein at least part is performed in a continuous mode, weight hourly space velocities ranging from 5 to 7 per hour are chosen for the contacting of the gas stream in step (II) with a catalyst according to the present invention.

As regards the specific weight hourly space velocities according to specific embodiments of the inventive process for the conversion of oxygenates to olefins, said weight hourly space velocities are specifically adjusted in function of the conversion of the one or more oxygenates comprised in the gas stream provided in step (I) of the inventive process, and in particular adjusted such that a certain level of conversion comprised in a specific range is achieved. Thus, according to the particular and specific embodiments of the inventive process, the weight hourly space velocities may be adjusted such that the conversion of the one or more oxygenates lies in the range of from 50 to 99.9%. According to the present invention, weight hourly space velocities are specific according to the particular and specific embodiments of the inventive process wherein the conversion of the oxygenates lies in the range of from 70 to 99.5%, more specifically from 90 to 99%, more specifically from 95 to 98.5%, more specifically from 96 to 98%, and even more specifically from 96.5 to 97.5%. According to the inventive process, it is however yet further specific that the weight hourly space velocity under which the gas stream in step (II) is contacted with a catalyst according to the present invention is adjusted to assure full conversion of the one or more oxygenates, i.e. a conversion of from 96.5 to 99.9% or more thereof, more specifically a conversion of the one or more oxygenates of from 97.5 to 99.9% or more thereof, more specifically of from 98 to 99.9% or more thereof, more specifically of from 99 to 99.9% or more thereof, and more specifically of from 99.5 to 99.9% or more relative to the conversion of the one or more oxygenates.

Therefore, embodiments of the inventive process are further specific wherein the weight hourly space velocity (WHSV) of the gas stream in step (II) ranges from 0.5 to 50 $h^{-1}$.

EXAMPLES

Determination of the Crystallinity

The crystallinity of the zeolitic materials in the present examples was determined by XRD analysis, wherein the crystallinity of a given material is expressed relative to a reference zeolitic material wherein the reflecting surfaces of the two zeolitic materials are compared. The reference zeolitic materials were commercial H-ZSM-5 at an $SiO_2/Al_2O_3$ ratio of 100 or 250. The determination of the crystallinities was performed on a D8 Advance series 2 diffractometer from Bruker AXS. The diffractometer was configured with an opening of the divergence aperture of 0.1° and a Lynxeye detector. The samples as well as the reference zeolitic material were measured in the range from 21° to 25° (2 Theta). After baseline correction, the reflecting surfaces were determined by making use of the evaluation software EVA (from Bruker AXS). The ratios of the reflecting surfaces are given as percentage values.

FT-IR Measurements

The IR measurements in the present examples were performed on a Nicolet 6700 spectrometer. The zeolitic materials were pressed into a self-supporting pellet without the use of any additives. The pellet was introduced into a high vacuum cell placed into the IR instrument. Prior to the measurement the sample was pretreated in high vacuum (10-5 mbar) for 3 h at 300° C. The spectra were collected after cooling the cell to 50° C. The spectra were recorded in the range of 4000 $cm^{-1}$ to 1400 $cm^{-1}$ at a resolution of 2 $cm^{-1}$. The obtained spectra were represented by a plot having on the x axis the wavenumber ($cm^{-1}$) and on the y axis the absorbance (arbitrary units). For the quantitative determination of the band heights and the ratio between the bands a baseline correction was carried out. Changes in the 3000 to 3900 $cm^{-1}$ region were analyzed and for comparing multiple samples, the band at 1880±5 $cm^{-1}$ was taken as reference.

Water Adsorption/Desorption Measurements

Water adsorption/desorption isotherms in the present examples were performed on a VTI SA instrument from TA Instruments following a step-isotherm program. The experiment consisted of a run or a series of runs performed on a sample material that has been placed on the microbalance pan inside of the instrument. Before the measurement was started, the residual moisture of the sample was removed by heating the sample to 100° C. (heating ramp of 5° C./min) and holding it for 6 h under a nitrogen flow. After the drying program, the temperature in the cell was decreased to 25° C. and kept constant during the measurement. The microbalance was calibrated, and the weight of the dried sample was balanced (maximum mass deviation 0.01 wt.-%). Water uptake of a sample was measured as the increase in weight compared to the dry sample. First, an adsorption curve was measured by increasing the relative humidity (RH) (expressed as weight-% water in the atmosphere inside of the cell) to which the sample was exposed and measuring the water uptake by the sample as equilibrium. The RH was increased with a step of 10% from 5% to 85% and at each step the system controlled the RH and monitored the weight of the sample until reaching the equilibrium conditions after the sample and recording the weight uptake. The total adsorbed water of the sample was taken after the sample was exposed to the 85 weight-% RH. During the desorption measurement, the RH was decreased from 85 weight-% to 5 weight-% with a step of 10% and the change in the weight of the sample (water uptake) was monitored and recorded.

Determination of the Crush Strength of the Moldings

The crush strength in the present examples is to be understood as determined via a crush strength test machine Z2.5/TS1S, supplier Zwick GmbH & Co., D.89070 Ulm, Germany. As to the fundamentals of this machine and its operation, reference is made to the respective instructions handbook "Register 1: Betriebsanleitung/Sicherheitshandbuch für die Material-Prüfmaschine Z2.5/TS1S", version 1.5, December 2001 by Zwick GmbH & Co. Technische Dokumentation, August-Nagel-Strasse 11, D-89079 Ulm, Germany. With said machine, a given (final) strand as prepared in Examples 5 to 11, having a diameter of 2.5 mm, is subjected to an increasing force via a plunger having a diameter of 3 mm until the strand is crushed. The force at which the strand crushes is referred to as the crushing strength of the strand. The machine is equipped with a fixed horizontal table on which the strand is positioned. A plunger which is freely movable in vertical direction actuates the strand against the fixed bed table. The apparatus was operated with a preliminary force of 0.5 N, a shear rate under preliminary force of 10 mm/min and a subsequent testing rate of 1.6 mm/min. The vertically movable plunger was connected to a load cell for force pick-up and, during the measurement, moved toward the fixed turntable on which the molding (strand) to be investigated is positioned, thus actuating the strand against the table. The plunger was applied to the strands perpendicularly to their longitudinal axis. Controlling the experiment was carried out by means of a computer which registered and evaluated the results of the measurements. The values obtained are the mean value of the measurements for 25 strands in each case.

Reference Example 1

Synthesis of ZSM-5 Zeolite at an $SiO_2:Al_2O_3$ Molar Ratio of 100

Tetraethylorthosilicate (757 g) was stirred in a four-necked flask. Water (470 g) and tetrapropylammonium hydroxide (40 wt % in water, 366 g) were added. The mixture was stirred for 60 minutes during which the temperature rose to 60° C. This was due to the hydrolysis of tetraethylorthosilicate resulting in the formation of ethanol. The ethanol was removed via distillation until a sump temperature of 95° C. was reached. Thereby 817 g of ethanol were removed from the mixture. The mixture was then allowed to cool to 40° C. while stirring, 817 g of water were added and the resulting gel was filled into an autoclave. A solution of aluminum sulfate octadecahydrate (24.2 g) and water (40 g) were added to the autoclave. The autoclave was closed and heated to 170° C.

After stirring the gel at 170° C. for 48 h the autoclave was cooled to ambient temperature and the mixture was removed. It was treated with nitric acid (10 wt % in water, 173 g) until a pH value of 7.3 was reached. The resulting suspension was filtered. The filter cake was washed three times with water (1,000 mL each), dried (4 h, 120° C.) and calcined (5 h, 500° C.), to afford 217 g of ZSM-5. The size of the primary particles as determined by SEM was in the range of from 100 to 200 nm.

Elemental Analysis:

| | |
|---|---|
| Si | 43.5 wt.-% |
| Al | 0.87 wt.-% |
| Na | <100 ppm |
| K | <100 ppm |

Thus, according to the chemical analysis, the calcined material displayed an $SiO_2:Al_2O_3$ molar ratio of 96.

FIG. 1A shows the XRD of the crystalline product obtained from the synthesis of Reference Example 1, displaying the line pattern typical for the MFI framework structure. The crystallinity as determined according to Reference Example 1 was 98%.

Figure 1B:
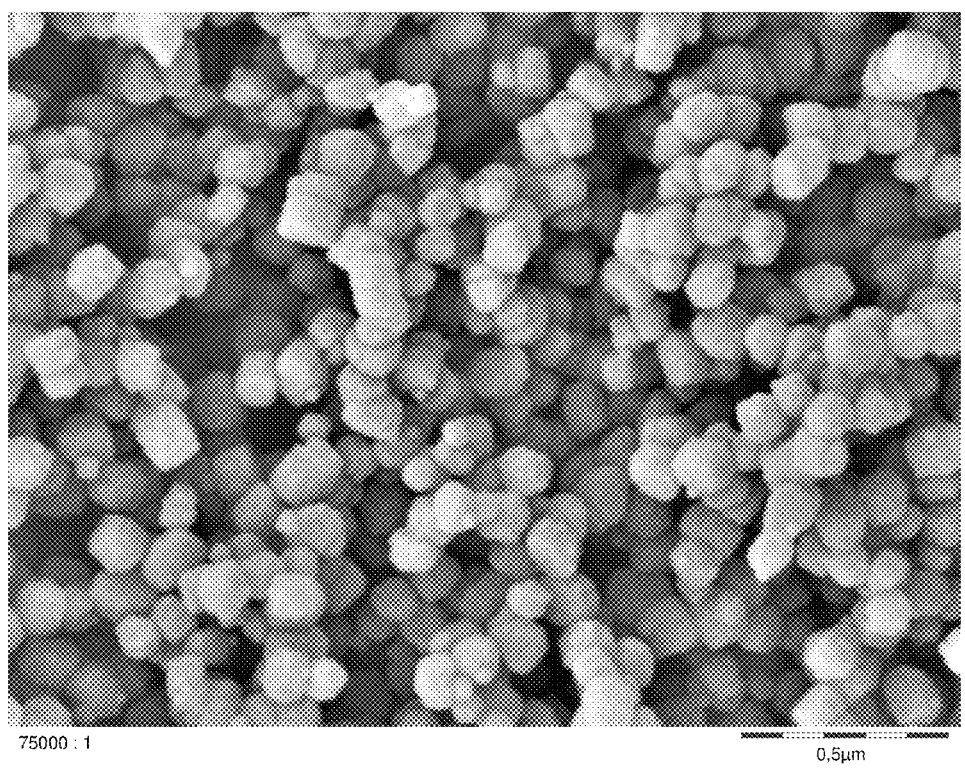
FIGS. 1B, 2B, 3B, and 4B respectively show a scanning electron micrograph (SEM) of the ZSM-5 powder which was obtained according to Reference Examples 1-4, respectively, using a magnification of 75,000:1 as indicated at the lower left hand corner of the image. At the lower right hand corner of the SEM micrographs, a unit length corresponding to 0.5 µm in the image is indicated as a checkered bar with 5 subunits of 0.1 µm, respectively.

FIG. 1B shows the electron micrograph of the product as obtained from SEM at a magnification of $75 \times 10^4$. As may be taken from the micrograph, practically only spherical primary particles are observed even at this high degree of magnification, wherein the size of the primary particles was determined to lie in the range of from 100-170 nm.

The material displayed a BET surface area of 426 $m^2/g$. The pore volume was determined to be 0.17 $cm^3/g$ at $p/p_0=0.302$ and the median pore width to be 0.58 nm as respectively determined via Argon adsorption using the Horvath-Kawazoe method. The total intrusion volume determined according to Hg porosimetry according to DIN 66133 was 1.24 ml/g (milliliter/gram), the respective total pore area 40.5 $m^2/g$.

Temperature programmed desorption of ammonia afforded values of 0.43 mmol/g when conducted at 152° C. and of 0.24 mmol/g when conducted at 378° C.

The material had a water uptake of 6.3 wt. % at a relative humidity of 85%.

Figure 1C:
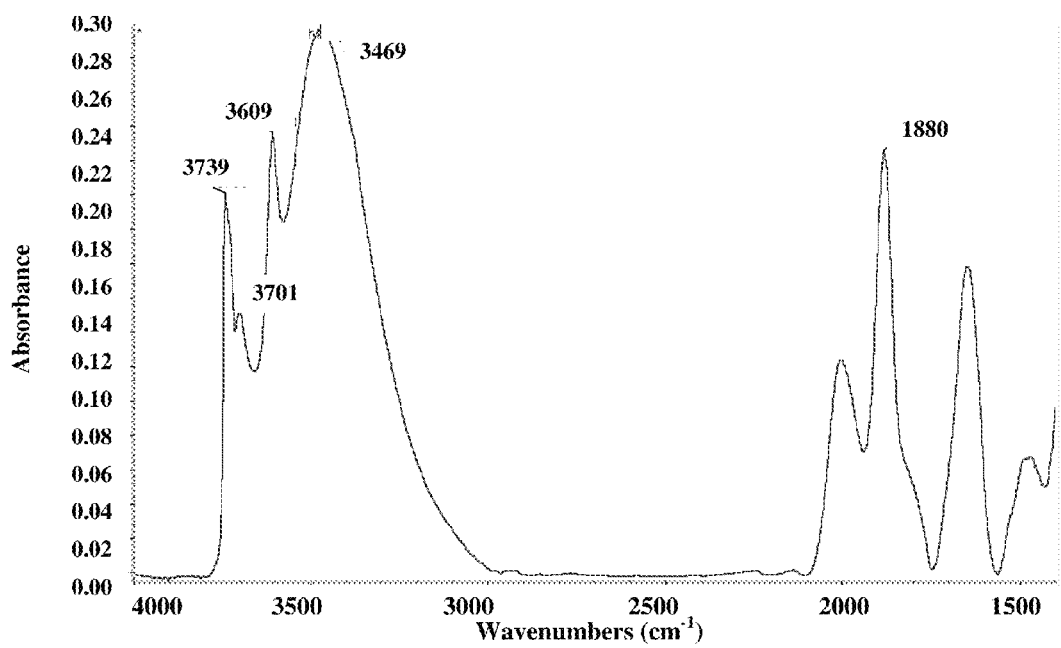

FIG. 1C shows the IR-OH bands of the sample obtained according to Reference Example 1. The band regions along with the band heights are as follows:

| Region of OH band | Assignment | Band Height |
|---|---|---|
| 3739 $cm^{-1}$ | external acid sites, i.e. "surface silanol" | 0.22 |
| 3701 $cm^{-1}$ | Lewis acid sites from extraframework Al | 0.16 |
| 3609 $cm^{-1}$ | Lewis acid sites from extraframework Al | 0.26 |
| 3469 $cm^{-1}$ | internal Broensted acid sites, i.e. "silanol nests" | 0.32 |

Accordingly, the IR-band ratio of the absorbance intensity for the silanol nests to the surface silanol amounts to 1.45.

Reference Example 2

Synthesis of ZSM-5 Zeolite at an $SiO_2:Al_2O_3$ Molar Ratio of 250

Tetraethylorthosilicate (757 kg) was stirred in a vessel. Water (470 kg) and tetrapropylammonium hydroxide (40 wt % in water, 333 kg) were added. The mixture was stirred for 60 minutes during which the temperature rose to 60° C. This was due to the hydrolysis of tetraethylorthosilicate resulting in the formation of ethanol. The ethanol was removed via distillation until a sump temperature of 95° C. was reached. Thereby 832 kg of ethanol were removed from the mixture. 832 kg of water and a solution of aluminum sulfate octadecahydrate (9.4 kg) and water (20 kg) were added to the vessel. The vessel was closed and heated to 150° C.

After stirring the gel at 150° C. for 24 h the autoclave was cooled to ambient temperature and the mixture was removed. It was treated with nitric acid (10 wt % in water) until a pH value of 7.1 was reached. The resulting suspension was filtered. The filter cake was washed with water and dried (120° C.). The dry powder was ground and subsequently calcined (5 h, 500° C.).

Elemental Analysis:

| | |
|---|---|
| Si | 43.5 wt.-% |
| Al | 0.36 wt.-% |
| Na | <100 ppm |
| K | <100 ppm |

Thus, according to the chemical analysis, the calcined material displayed an $SiO_2:Al_2O_3$ molar ratio of 233.

Figure 2A:
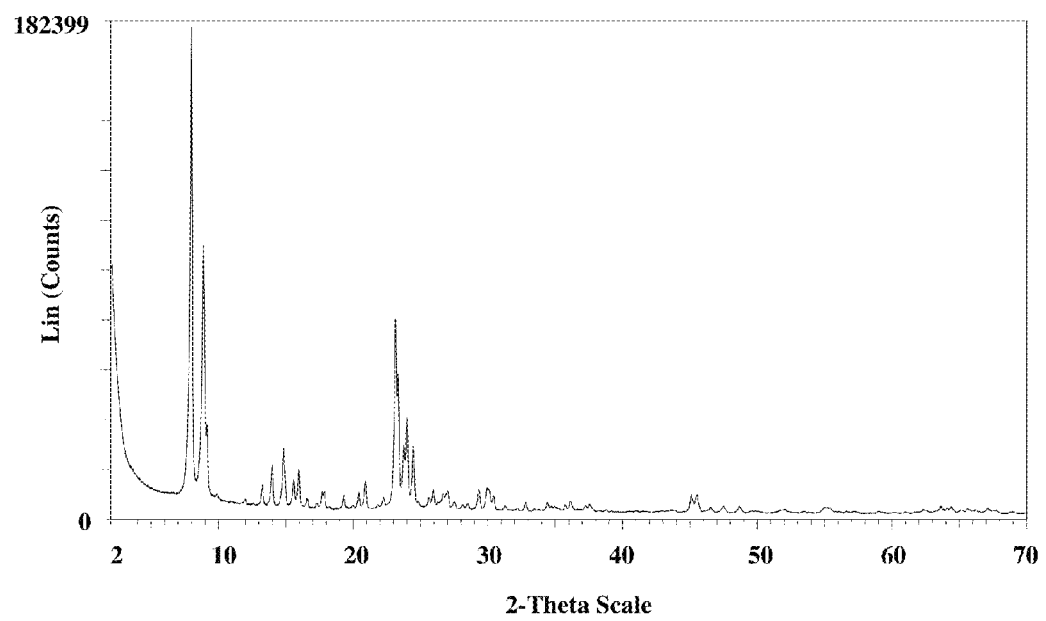
Figure 2B:
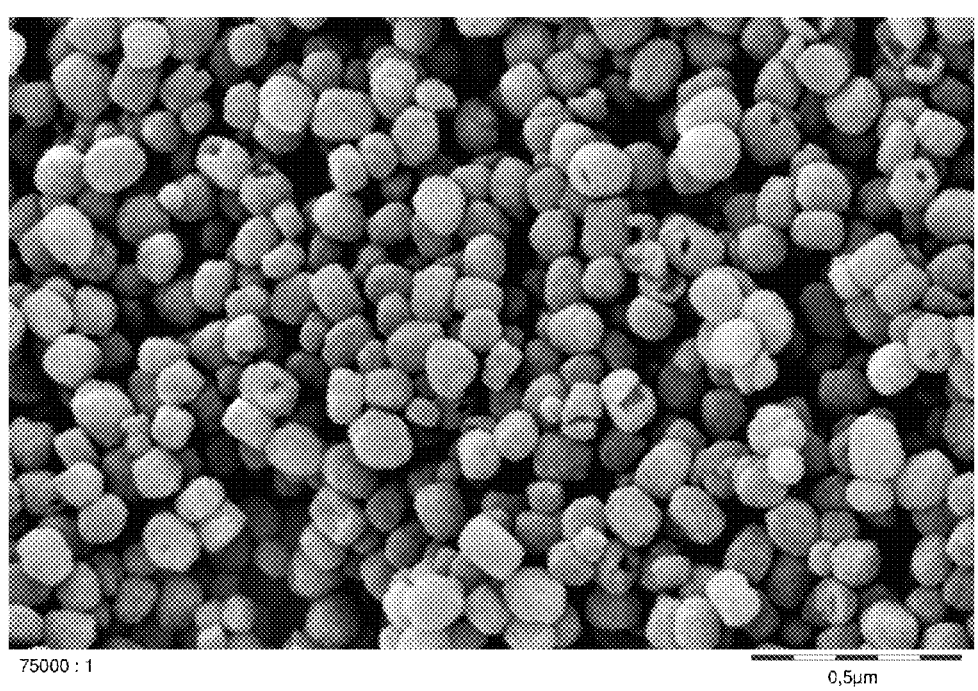

FIG. 2A shows the XRD of the crystalline product obtained from the synthesis of Reference Example 2, displaying the line pattern typical for the MFI framework structure. The crystallinity as determined according to Reference Example 1 was 96%. FIG. 2B shows the electron micrograph of the product as obtained from SEM at a magnification of $75 \times 10^4$. As may be taken from the micrograph, practically only spherical primary particles are observed even at this high degree of magnification, wherein the size of the primary particles was determined to lie in the range of from 50-150 nm.

The material displayed a BET surface area of 441 m²/g. The pore volume was determined to be 0.18 cm³/g at $p/p_0=0.301$ and the median pore width to be 0.54 nm as respectively determined via Argon adsorption using the Horvath-Kawazoe method. The total intrusion volume determined according to Hg porosimetry according to DIN 66133 was 1.45 ml/g (milliliter/gram), the respective total pore area 71.3 m²/g.

Temperature programmed desorption of ammonia ($NH_3$-TPD) afforded values of 0.24 mmol/g when conducted at 107° C. and of 0.12 mmol/g when conducted at 343° C.

The material had a water uptake of 7.1 wt. % at a relative humidity of 85%.

Figure 2C:
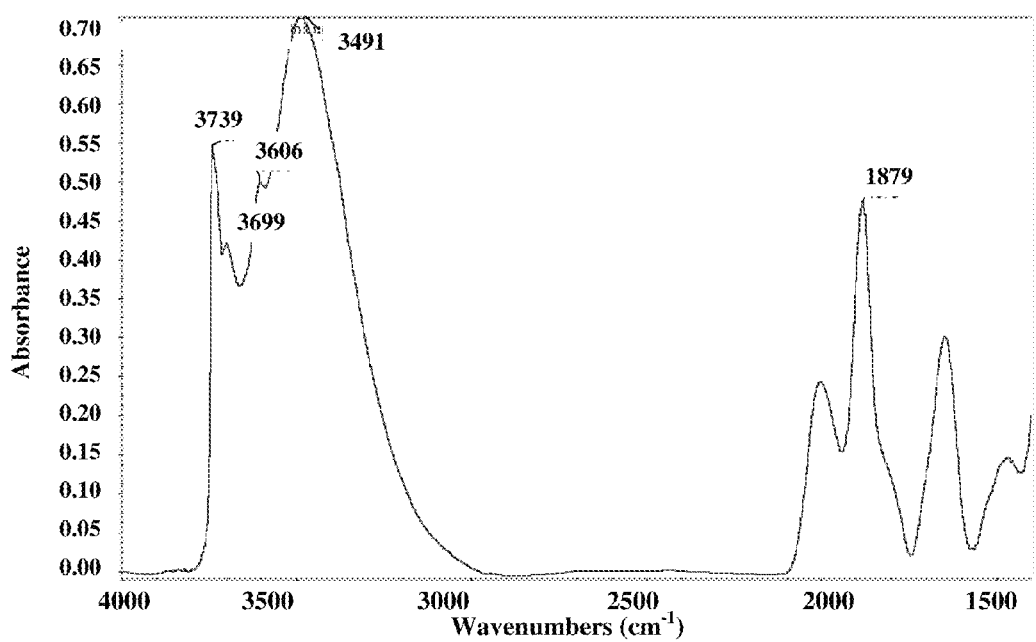

FIG. 2C shows the IR-OH bands of the sample obtained according to Reference Example 2. The band regions along with the band heights are as follows:

| Region of OH band | Assignment | Band Height |
|---|---|---|
| 3739 cm⁻¹ | external acid sites, i.e. "surface silanol" | 0.55 |
| 3699 cm⁻¹ | Lewis acid sites from extraframework Al | 0.43 |
| 3606 cm⁻¹ | Lewis acid sites from extraframework Al | 0.52 |
| 3491 cm⁻¹ | internal Broensted acid sites, i.e. "silanol nests" | 0.75 |

Accordingly, the IR-band ratio of the absorbance intensity for the silanol nests to the surface silanol amounts to 1.36.

Reference Example 3

Synthesis of ZSM-5 Zeolite at an $SiO_2:Al_2O_3$ Molar Ratio of 320

Tetraethylorthosilicate (757 g) was stirred in a four-necked flask. Water (470 g) and tetrapropylammonium hydroxide (40 wt % in water, 333 g) were added. The mixture was stirred for 60 minutes during which the temperature rose to 60° C. This was due to the hydrolysis of tetraethylorthosilicate resulting in the formation of ethanol. The ethanol was removed via distillation until a sump temperature of 95° C. was reached. Thereby 805 g of ethanol were removed from the mixture. The mixture was then allowed to cool to 40° C. while stirring, 805 g of water were added and the resulting gel was filled into an autoclave. A solution of aluminum sulfate octadecahydrate (7.6 g) and water (25 g) were added to the autoclave. The autoclave was closed and heated to 170° C.

After stirring the gel at 170° C. for 24 h the autoclave was cooled to ambient temperature and the mixture was removed. It was treated with nitric acid (10 wt % in water, 203 g) until a pH value of 7.6 was reached. The resulting suspension was filtered. The filter cake was washed three times with water (1000 mL each), dried (4 h, 120° C.) and calcined (5 h, 500° C.), thus affording 222 g of calcined zeolite ZSM-5.

Elemental Analysis:

| | |
|---|---|
| Si | 44 wt.-% |
| Al | 0.26 wt.-% |
| Na | <100 ppm |
| K | <100 ppm |

Thus, according to the chemical analysis, the calcined material displayed an $SiO_2:Al_2O_3$ molar ratio of 325.

Figure 3A:
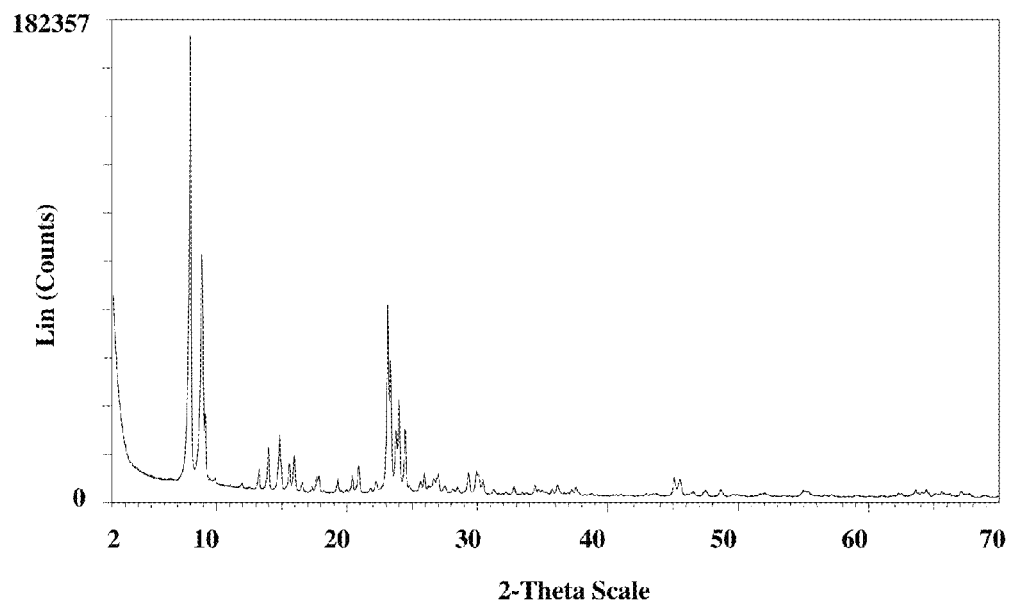
Figure 3B:
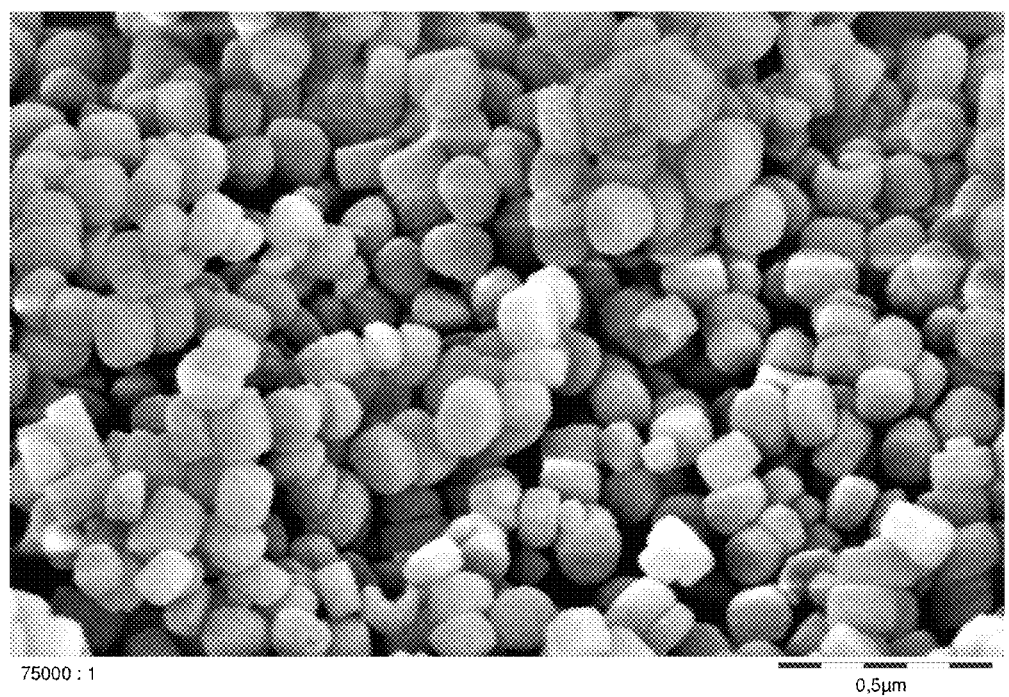

FIG. 3A shows the XRD of the crystalline product obtained from the synthesis of Example 1, displaying the line pattern typical for the MFI framework structure. FIG. 3B shows the electron micrograph of the product as obtained from SEM at a magnification of $75 \times 10^4$. As may be taken from the micrograph, practically only spherical primary particles are observed even at this high degree of magnification, wherein the size of the primary particles was determined to lie in the range of from 100-200 nm.

The material displayed a BET surface area of 442 m²/g. The pore volume was determined to be 0.18 cm³/g at $p/p_0=0.301$ and the median pore width to be 0.58 nm as respectively determined via Argon adsorption using the Horvath-Kawazoe method. Temperature programmed desorption of ammonia ($NH_3$-TPD) afforded values of 0.19 mmol/g when conducted at 108° C. and of 0.067 mmol/g when conducted at 340° C.

Reference Example 4

Water-Treatment of ZSM-5 Zeolite at an SiO$_2$:Al$_2$O$_3$ Molar Ratio of 100

Starting from the calcined powder obtained according to Reference Example 1, a post-treatment stage was performed as follows:

100 g of the calcined zeolitic powder obtained according to Reference Example 1 were suspended in 2000 g of deionized water. The mixture was filled in a vessel and the vessel was closed (pressure-tight). Then, the mixture was heated to a temperature of 145° C. within 1.5 h and kept at this temperature under autogenous pressure (about 4 bar) for 8 h. The water-treated powder was subjected to filtration and washed with deionized water. The obtained filter cake was dried at 120° C. for 4 h. Subsequently, the dried material was heated under air to a temperature of 500° C. within 4 h and kept at this temperature for 5 h. The yield thereafter was 85 g.

The thus obtained water-treated zeolitic powder had a Si content of 45 wt. %, an Al content of 0.87 wt. % which correspond to an SiO$_2$:Al$_2$O$_3$ molar ratio of 99.

Figure 4A:
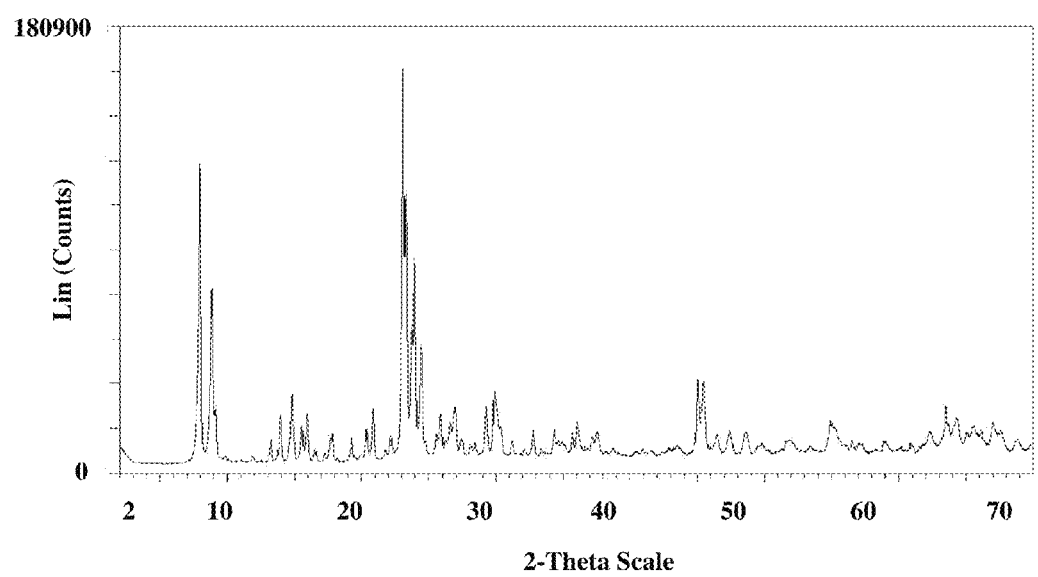

The degree of crystallization determined via XRD was 101-114%. The XRD of the material is shown in FIG. 4A. Thus, the inventive water treatment caused an increase from a value of 98% (cf. Reference Example 1) to a value of 101-114%.

Figure 4B:
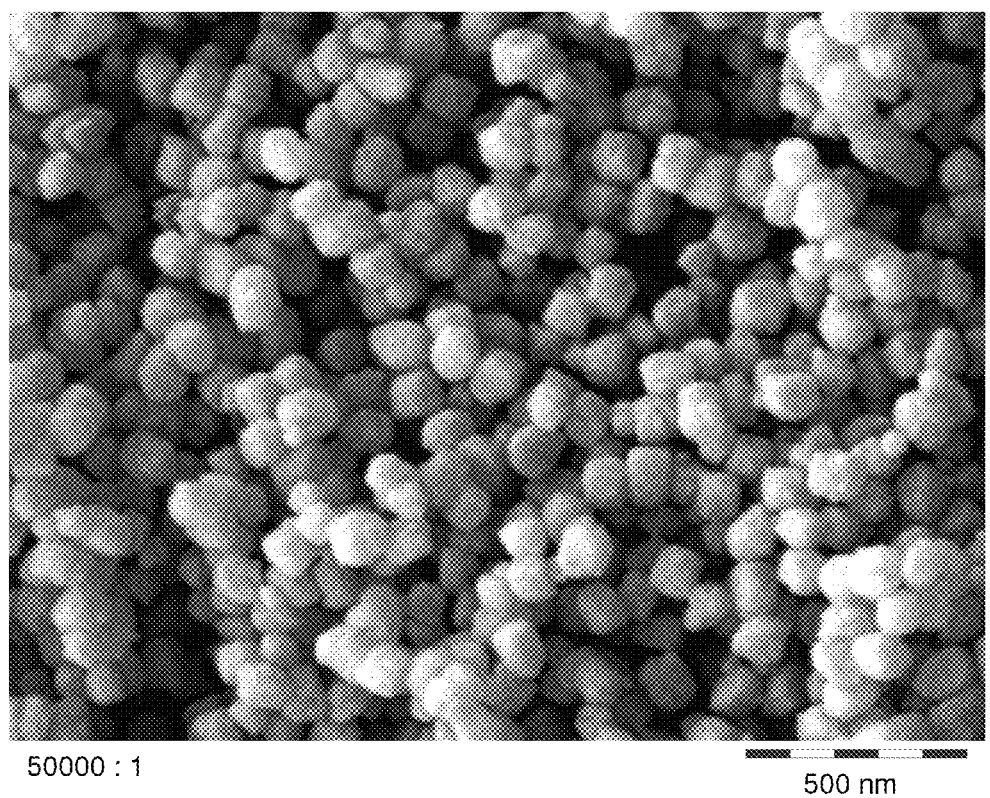

FIG. 4B shows the electron micrograph of the product as obtained from SEM at a magnification of 50×10$^4$. As may be taken from the micrograph, practically only spherical primary particles are observed even at this high degree of magnification, wherein the size of the primary particles was determined to lie in the range of from 70-150 nm.

The powder had a multipoint BET specific area determined via nitrogen adsorption at 77K according to DIN 66133 of 427 m$^2$/g. The pore volume was determined to be 0.17 cm$^3$/g at p/p$_0$=0.281 and the median pore width to be 0.51 nm as respectively determined via Argon adsorption using the Horvath-Kawazoe method. The total intrusion volume determined according to Hg porosimetry according to DIN 66133 was 1.11 ml/g (milliliter/gram), the respective total pore area 40.7 m$^2$/g.

The total amount of adsorbed water as determined was 3.8-4.1 wt. % (compared to 6.3 wt. % of the starting material as described in Reference Example 1). Therefore, it is clearly shown that the inventive water treatment increases the hydrophobicity of the powder.

The IR spectrum of the powder obtained according to Reference Example 4 is shown in FIG. 4C.

The band regions of the powder according to Reference Example 4 along with the band heights are as follows:

| Region of OH band | Assignment | Band Height |
|---|---|---|
| 3741 cm$^{-1}$ | external acid sites, i.e. "surface silanol" | 0.26 |
| ~3700 cm$^{-1}$ | Lewis acid sites from extraframework Al | value too low to be measured |
| 3609 cm$^{-1}$ | Lewis acid sites from extraframework Al | 0.32 |
| 3476 cm$^{-1}$ | internal Broensted acid sites, i.e. "silanol nests" | 0.26 |

Accordingly, the IR-band ratio of the absorbance intensity for the silanol nests to the surface silanol amounts to 1.00.

Comparative Example 5

Shaping of ZSM-5 Zeolite from Reference Example 1

ZSM-5 powder (100 g) obtained from Reference Example 1 was mixed with Pural SB (86.5 g), formic acid (2.6 g in 20 mL water) and Walocel (5 g). The masses of the raw materials were chosen in a way as to yield a zeolite-to-binder ratio of 60:40 in the resulting calcined shaped bodies. The mixture was homogenized in a kneading machine by the addition of water (100 g). The obtained plastic mixture was formed to strands (Ø2.5 mm) using a strand press (pressure ~100 bar). The strands were dried (16 h, 120° C.) and calcined (4 h, 500° C.), thus obtaining extrudates having a cutting hardness of 11.1N.

Elemental Analysis:

| | |
|---|---|
| Si | 25.6 wt.-% |
| Al | 19.6 wt.-% |

The BET surface area of the extrudates was determined to 362 m$^2$/g, and the pore volume as obtained by Hg-Porosimetry to 0.46 cm$^3$/g, the respective total pore area 117.0 m$^2$/g.

Comparative Example 6

Shaping of ZSM-5 Zeolite from Reference Example 2

ZSM-5 powder (100 g) obtained from Reference Example 2 was mixed with Pural SB (86.5 g), formic acid (2.6 g in 20 mL water) and Walocel (5 g). The masses of the raw materials were chosen in a way as to yield a zeolite-to-binder ratio of 60:40 in the resulting calcined shaped bodies. The mixture was homogenized in a kneading machine by the addition of water (83 g). The obtained plastic mixture was formed to strands (Ø2.5 mm) using a strand press (pressure ~100 bar). The strands were dried (16 h, 120° C.) and calcined (4 h, 500° C.), thus obtaining extrudates having a cutting hardness of 21.6 N.

Elemental Analysis:

| | |
|---|---|
| Si | 25.7 wt.-% |
| Al | 19.1 wt.-% |

The BET surface area of the extrudates was determined to 374 m$^2$/g, and the pore volume as obtained by Hg-Porosimetry to 0.36 cm$^3$/g, the respective total pore area 119.5 m$^2$/g.

Example 7

Impregnation of ZSM-5 Zeolite from Reference Example 1 with Magnesium and Shaping Thereof ZSM-5 powder from Reference Example 1 was spray impregnated with a magnesium nitrate solution. The amount of magnesium nitrate was chosen in a way as to obtain a zeolite with 4 wt % of Mg after calcination. To this effect, zeolite powder (98.2 g) obtained from Reference Example 1 was placed into a round-bottomed flask that was connected to a rotary evaporator. Magnesium nitrate (44.0 g) was solubilized in water to yield 77 mL of a solution. 68.9 mL of the solution were slowly sprayed on the rotating zeolite using a spray nozzle (100 l/h N$_2$ stream). This corresponds to 90% of the maximum water uptake capacity of the zeolite. After the complete solution was sprayed on the zeolite, the latter was allowed to rotate for 10 min. The treated powder was dried (16 h, 120° C.), calcined (4 h, 500° C.), milled and sieved (1 mm size).

Elemental Analysis:

| | |
|---|---|
| Mg | 4.0 wt % |

The Mg-impregnated zeolite was shaped to extrudates exhibiting a zeolite-to-binder ratio of 60/40 in their calcined form. ZSM-5 powder (100 g) was mixed with Pural SB (86.5 g), formic acid (2.6 g in 20 mL water) and Walocel (5 g). The mixture was homogenized in a kneading machine by the addition of water (95 g). The obtained plastic mixture was formed to strands (Ø2.5 mm) using a strand press (pressure ~150 bar). The strands were dried (16 h, 120° C.) and calcined (4 h, 500° C.), thus obtaining extrudates having a cutting hardness of 10.2 N.

Elemental Analysis:

| | |
|---|---|
| Si | 23.8 wt.-% |
| Al | 19.4 wt.-% |
| Mg | 2.3 wt.-% |

The BET surface area of the extrudates was determined to 309 m$^2$/g, and the pore volume as obtained by Hg-Porosimetry to 0.84 cm$^3$/g, the respective total pore area 102.9 m$^2$/g.

Example 8

Impregnation of ZSM-5 Zeolite from Reference Example 2 with Magnesium and Shaping Thereof ZSM-5 powder from Reference Example 2 was spray impregnated with a magnesium nitrate solution. The amount of magnesium nitrate was chosen in a way as to obtain a zeolite with 4 wt % of Mg after calcination. To this effect, zeolite powder (120 g) obtained from Reference Example 2 was placed into a round-bottomed flask that was connected to a rotary evaporator. Magnesium nitrate (53.8 g) was solubilized in water to yield 82 mL of a solution. 73 mL of the solution were slowly sprayed on the rotating zeolite using a spray nozzle (100 l/h N$_2$ stream). This corresponds to 90% of the maximum water uptake capacity of the zeolite. After the complete solution was sprayed on the zeolite, the latter was allowed to rotate for 10 min. The treated powder was dried (16 h, 120° C.), calcined (4 h, 500° C.), milled and sieved (1 mm size).

Elemental Analysis:

| | |
|---|---|
| Mg | 4.1 wt % |

The BET surface area of the impregnated ZSM-5 powder was determined to 318 m$^2$/g.

The Mg-impregnated zeolite was then shaped to extrudates exhibiting a zeolite-to-binder ratio of 60/40 in their calcined form. To this effect, the impregnated ZSM-5 powder (100 g) was mixed with Pural SB (86.5 g), formic acid (2.6 g in 20 mL water) and Walocel (5 g). The mixture was homogenized in a kneading machine by the addition of water (85 g). The obtained plastic mixture was formed to strands (Ø2.5 mm) using a strand press (pressure ~130 bar). The strands were dried (16 h, 120° C.) and calcined (4 h, 500° C.), thus obtaining extrudates having a cutting hardness of 11.0 N.

Elemental Analysis:

| | |
|---|---|
| Si | 24.3 wt.-% |
| Al | 19.2 wt.-% |
| Mg | 2.4 wt.-% |

The BET surface area of the extrudates was determined to 310 m$^2$/g, and the pore volume as obtained by Hg-Porosimetry to 0.67 cm$^3$/g.

Example 9

Impregnation of Water-Treated ZSM-5 Zeolite from Reference Example 4 with Magnesium and Shaping Thereof ZSM-5 powder from Reference Example 4 was spray impregnated with a magnesium nitrate solution. The amount of magnesium nitrate was chosen in a way as to obtain a zeolite with 4 wt % of Mg after calcination. To this effect, the zeolite powder (100 g) was placed into a round-bottomed flask that was connected to a rotary evaporator. Magnesium nitrate (44.8 g) was solubilized in water. 61.2 mL of the solution were slowly sprayed on the rotating zeolite using a spray nozzle (100 l/h N$_2$ stream). This corresponds to 90% of the maximum water uptake capacity of the zeolite. After the complete solution was sprayed on the zeolite, the latter was allowed to rotate for 10 min. The treated powder was dried (16 h, 120° C.), calcined (4 h, 500° C.), milled and sieved (1 mm size).

The obtained powder has an Mg content of 3.9 wt %.

Mg-ZSM-5 powder (98.9 g) was mixed with Pural SB (90.3 g), formic acid (2.7 g in 20 mL water) and Walocel (5 g). The masses of the raw materials were chosen in a way as to yield a zeolite-to-binder ratio of 60:40 in the resulting calcined shaped bodies. The mixture was homogenized in a kneading machine by the addition of water (90 g). The obtained plastic mixture was formed to strands (Ø2.5 mm) using a strand press (pressure ~100 bar). The strands were dried (16 h, 120° C.) and calcined (4 h, 500° C.). They were split to 1.6-2.0 mm fractions using a sieving machine equipped with two steel balls (Ø2 cm, 258 g/ball) prior to application in the conversion of methanol to olefins.

The obtained extrudates had a Si content of 23.7 wt. %, an Al content of 20.7 wt. %, an Mg content of 2.3 wt % and a multipoint BET specific area determined via nitrogen adsorption at 77 K according to DIN 66133 of 307 m$^2$/g.

The crush strength of the moldings as determined according to the method using a crush strength test machine Z2.5/TS1S as described in Reference Example 4 was 8.7 N.

The total intrusion volume determined according to Hg porosimetry according to DIN 66133 was 0.88 mL/g (milliliter/gram), the respective total pore area 124.7 m$^2$/g.

Comparative Example 10

Shaping of a Commercial ZSM-5 Zeolite with an SiO$_2$:Al$_2$O$_3$ Molar Ratio of 100

For comparison to the inventive materials, the procedure of Comparative Example 5 was repeated using a commercial ZSM-5 zeolite (PZ/2-100 H from ZEOCHEM®) having an SiO$_2$:Al$_2$O$_3$ molar ratio of 100. Analysis of the zeolitic material prior to conducting the procedure afforded a BET surface area of 412 m$^2$/g. The pore volume was determined to be 0.16 cm$^3$/g at p/p$_0$=0.304 and the median pore width to be 0.55 nm as respectively determined via Argon adsorption using the Horvath-Kawazoe method. Temperature programmed desorption of ammonia (NH$_3$-TPD) afforded values of 0.41 mmol/g when conducted at 161° C. and of 0.25 mmol/g when conducted at 355° C. The size of the primary particles of the commercial ZSM-5 zeolite as determined by SEM were shown to lie in the range of from 200-500 nm.

After repeating the procedure of Comparative Example 5 using the commercial ZSM-5 zeolite, the extrudates which were obtained were shown to have a cutting hardness of 26.4 N.

Elemental Analysis:

| Si | 25.9 wt.-% |
|---|---|
| Al | 19.7 wt.-% |

The BET surface area of the extrudates was determined to 310 m$^2$/g, and the pore volume as obtained by Hg-Porosimetry to 0.36 cm$^3$/g.

Comparative Example 11

Impregnation of a Commercial ZSM-5 Zeolite with Magnesium and Shaping Thereof

For further comparison, the procedure of Example 7 was repeated using the commercial ZSM-5 zeolite employed in Comparative Example 10, thus obtaining extrudates having a cutting hardness of 10.5 N.

Elemental Analysis:

| Si | 24.8 wt.-% |
|---|---|
| Al | 19.3 wt.-% |
| Mg | 2.2 wt.-% |

The BET surface area of the extrudates was determined to 293 m$^2$/g, and the pore volume as obtained by Hg-Porosimetry to 0.44 cm$^3$/g.

Example 12

Catalyst Testing in the Conversion of Methanol to Olefins

The extrudates obtained from Examples 7 to 9 and Comparative Examples 5, 6, 10, and 11 were respectively split to 1.6-2.0 mm fractions using a sieving machine equipped with two steel balls (Ø2 cm, 258 g/ball) for providing the respective catalyst sample. 2 g of each catalyst sample was then respectively diluted with 23 g of silicon carbide for affording the respective catalyst charge used in testing.

Methanol was evaporated, mixed with nitrogen to afford a gas stream containing 75 vol.-% methanol and 25 vol.-% nitrogen. Methanol in the gas stream was then converted to dimethylether in a heated pre-reactor (275° C.) charged with alumina split (34 mL). The resulting stream was then converted in a continuously operated, electrically heated tubular reactor that was charged with the respective zeolite catalyst (2 g, diluted with 23 g of SiC) to be tested. The MTO reaction was conducted at a temperature of 450-500° C. at a pressure (absolute) of 1-2 bar and at a weight hourly space velocity of 6 h$^{-1}$ based on the volume of methanol in the initial gas stream. The reaction was interrupted after the methanol conversion rate had fallen below 97%. The gaseous product mixture was analyzed by on-line gas chromatography, the results of which are displayed in the table below.

TABLE

Average selectivities and operation time at a methanol conversion rate of >97%.

| | Comp. Ex. 5 | Comp. Ex. 10 | Example 7 | Example 9 | Comp. Ex. 11 | Comp. Ex. 6 | Example 8 |
|---|---|---|---|---|---|---|---|
| SiO$_2$:Al$_2$O$_3$ ratio zeolite | | | ~100 | | | | 233 |
| Mg [wt.-%] | — | — | 2.3 wt.-% | 2.3 wt.-% | 2.2 wt.-% | — | 2.4 wt.-% |
| water treatment zeolite | no | no | no | yes | no | no | no |
| water adsorp. zeolite [%] | 6.3 | n.a. | 7.1 | 3.8-4.1 | n.a. | 7.1 | 7.1 |
| IR band ratio of zeolite | 1.45 | n.a. | 1.36 | 1.00 | n.a. | 1.36 | 1.36 |
| operation time | 26.0 | 20.7 | 124.0 | 209 | 85.0 | 15.0 | 140 |
| selectivity [%]: | | | | | | | |
| Ethylene | 9.9 | 9.4 | 7.3 | 7.7 | 8.8 | 9.6 | 4.1 |
| Propylene | 22.6 | 22.0 | 35.5 | 40.7 | 34.7 | 26.7 | 39.8 |
| Butylene | 11.9 | 12.4 | 24.1 | 26.3 | 25.4 | 17.3 | 22.5 |
| C$_4$-paraffins | 12.2 | 8.3 | 3.0 | 1.9 | 3.1 | 8.6 | 2.6 |
| C$_{5+}$ (mixture) | 13.3 | 26.9 | 24.1 | 15.4 | 18.3 | 15.1 | 25.1 |
| Aromatics | 21.6 | 14.5 | 4.2 | 5.9 | 5.9 | 16.2 | 4.2 |
| light gas | 8.4 | 6.6 | 1.8 | 2.0 | 3.8 | 6.5 | 1.7 |

As may be taken from the results for Comparative Examples 5 and 10 in the Table above, the use of sodium-free synthetic procedure for the production of the catalyst in Comparative Example 5 leads to a slight improvement in the operation time at which conversions of >97% based on methanol may be achieved. The additional use of Mg in Comparative Example 11, however, allows for a considerable improvement of the operation time, such that when compared to Comparative Example 10 an improvement of the magnitude of a factor of about 4 is observed. When applied to the catalysts obtained from sodium-free synthesis, however, the use of Mg unexpectedly leads to an improvement of the operation time by a factor of 6 as may be taken from the inventive Example 7 when compared to Comparative Example 5.

Accordingly, it has quite surprisingly been found that a strong synergetic effect is at work in the catalysts according to the present invention due to the specific use of Mg in a zeolitic material as obtainable from a sodium-free synthetic procedure. Said highly unexpected technical effect may also be observed for materials having higher $SiO_2:Al_2O_3$ molar ratios. Thus, the inventive catalyst of Example 8 displaying an $SiO_2:Al_2O_3$ molar ratio of 233 already affords an almost 10-fold improvement in operation time compared to the catalyst according to Comparative Example 6 having the same silica to alumina ratio, yet devoid of Mg.

Far more surprisingly, however, as may be taken from the results for the inventive process employing the extrudate according to Example 9, the use of a water treatment procedure for increasing the hydrophobicity of the zeolitic material leads to a considerable increase in the selectivities for both propylene and butylene. This effect is attributed to the higher hydrophobicity of the water-treated material due to the lower the water adsorption of the zeolitic material. Furthermore, a tremendous considerable increase in the lifetime of the catalyst is also observed for the water-treated zeolitic material contained in the extrudate of Example 9.

What is claimed is:

1. A process for the production of a zeolitic material having an MFI, MEL, and/or MWW-type framework structure comprising $YO_2$ and $X_2O_3$, wherein said process comprises
   (1) preparing a mixture comprising one or more sources for $YO_2$, one or more sources for $X_2O_3$, one or more solvents, and one or more organotemplates;
   (2) crystallizing the mixture obtained in step (1) to obtain a zeolitic material having an MFI, MEL and/or MWW-type framework structure; and
   (3) impregnating the zeolitic material obtained in step (2) with one or more elements selected from the group of alkaline earth metals;
   wherein Y is a tetravalent element, and X is a trivalent element,
   wherein the mixture crystallized in step (2) contains 3 wt.-% or less of one or more elements M based on 100 wt-% of $YO_2$, wherein M stands for sodium, and
   wherein the one or more organotemplates comprises one or more alkenyltrialkylammonium compounds selected from the group consisting of N—($C_2$-$C_5$)alkenyl-tri-($C_1$-$C_5$)alkylammonium compounds.

2. A process for the production of a zeolitic material having an MFI-type framework structure comprising $YO_2$ and $X_2O_3$, wherein said process comprises
   (1) preparing a mixture comprising one or more sources for $YO_2$, one or more sources for $X_2O_3$, and one or more solvents;
   (2) crystallizing the mixture obtained in step (1) to obtain a zeolitic material having an MFI-type framework structure; and
   (3) impregnating the zeolitic material obtained in step (2) magnesium;
   wherein Y is a tetravalent element, and X is a trivalent element, and
   wherein the mixture crystallized in step (2) contains 1 wt.-% or less of one or more elements M based on 100 wt-% of $YO_2$, wherein M stands for sodium.

3. The process of claim 1, wherein M comprises mixtures of sodium and potassium.

4. The process of claim 1, wherein in step (3) the zeolitic material is additionally impregnated with one or more elements selected from the group consisting of Ca, Ba, and Sr, and mixtures of two or more thereof.

5. The process of claim 1, wherein the $YO_2:X_2O_3$ molar ratio of the mixture prepared in step (1) ranges from 10 to 1,500.

6. The process of claim 1, wherein Y is selected from the group consisting of Si, Sn, Ti, Zr, Ge, and mixtures of two or more thereof.

7. The process of claim 1, wherein X is selected from the group consisting of Al, B, In, Ga, and mixtures of two or more thereof.

8. The process of claim 1, wherein the one or more solvents comprise one or more polar solvents.

9. The process of claim 1, wherein the mixture in step (1) further comprises one or more organotemplates.

10. The process of claim 9, wherein the one or more organotemplates comprises one or more tetraalkylammonium compounds selected from the group consisting of tetraethylammonium compounds, triethylpropylammonium compounds, diethyldipropylammonium compounds, ethyltripropylammonium compounds, tetrapropylammonium compounds, and mixtures of two or more thereof.

11. The process of claim 9, wherein the molar ratio of the total amount of the one or more organotemplates of the mixture obtained in step (1) to $YO_2$ ranges from 1:(0.1-30).

12. The process of claim 1, wherein the mixture according to step (1) further comprises one or more sources for $OH^{13}$.

13. The process of claim 12, wherein the $OH^-:YO_2$ molar ratio of the mixture obtained in step (1) ranges from 0.01 to 5.

14. The process of claim 1, wherein the crystallization in step (2) involves heating of the mixture.

15. The process of claim 1, wherein the crystallization in step (2) is conducted under solvothermal conditions.

16. The process of claim 1, wherein the crystallization in step (2) involves heating of the mixture for at least 3 h.

17. The process of claim 1, wherein after step (2) and prior to step (3) the process further comprises (2a) adjusting the pH of the product mixture obtained in (2) to a pH in the range of 5 to 9; and/or (2b) isolating the zeolitic material from the product mixture obtained in (2); and/or (2c) washing the zeolitic material; and/or (2d) drying and/or calcining the zeolitic material; and/or (2e) subjecting the zeolitic material to a hydrothermal treatment.

18. The process of claim 17, wherein the calcination in step (2d) is conducted at a temperature in the range of 300 to 850° C.

19. The process of claim 17, wherein the hydrothermal treatment in step (2e) is conducted under autogenous pressure.

20. The process of claim 17, wherein the hydrothermal treatment in step (2e) is conducted using an aqueous solvent system, wherein specifically the aqueous solvent system consists of water, specifically of distilled water.

21. The process of claim 17, wherein the hydrothermal treatment in step (2e) is conducted under heating.

22. The process of claim 17, wherein the hydrothermal treatment in step (2e) is conducted for a duration ranging from 2 to 72 h.

23. The process of claim 17, wherein the hydrothermally treated zeolitic material obtained in step (2e) displays a water uptake of 10.0 wt.-% or less.

24. The process of claim 1, wherein in step (3) the zeolitic material is impregnated with magnesium from 0.1 to 15 wt.-% based on the total weight of the zeolitic material.

25. A zeolitic material having an MFI-type framework structure comprising $YO_2$ and $X_2O_3$, wherein Y is a tetravalent element, and X is a trivalent element, wherein the zeolitic material contains 1 wt.-% or less of one or more elements M based on 100 wt.-% of $YO_2$, wherein M stands for sodium, wherein the zeolitic material further comprises magnesium, and wherein 95% by weight or more of the primary particles have a diameter of less than or equal to 1 µm.

26. The zeolitic material of claim 25, wherein the zeolitic material is obtainable and/or obtained by a process comprising (1) preparing a mixture comprising one or more sources for $YO_2$, one or more sources for $X_2O_3$, and one or more solvents; (2) crystallizing the mixture obtained in step (1) to obtain a zeolitic material having an MFI-type framework structure; and (3) impregnating the zeolitic material obtained in step (2) with magnesium; wherein Y is a tetravalent element, and X is a trivalent element, and wherein the mixture crystallized in step (2) contains 3 wt.-% or less of one or more elements M based on 100 wt.-% of $YO_2$, wherein M stands for sodium.

27. The zeolitic material of claim 25, wherein 90% or more of the primary particles are spherical.

28. The zeolitic material of claim 25, wherein 95% by weight or more of the primary particles have a diameter of from 5 to 800 nm.

29. The zeolitic material of claim 25, wherein M comprises mixtures of sodium and potassium.

30. The zeolitic material of claim 25, wherein the magnesium further comprised in the zeolitic material are contained in the zeolitic material in an amount ranging from 0.1 to 15 wt.-% based on the total weight of the zeolitic material.

31. The zeolitic material of claim 25, wherein the zeolitic mixture further comprises an alkaline earth metal that is selected from the group consisting of Ca, Ba, and Sr, and mixtures of two or more thereof.

32. The zeolitic material of claim 25, wherein the zeolitic material displays a $YO_2:X_2O_3$ atomic ratio of from 10 to 1,500.

33. The zeolitic material of claim 25, wherein Y is selected from the group consisting of Si, Sn, Ti, Zr, Ge, and mixtures of two or more thereof.

34. The zeolitic material of claim 25, wherein X is selected from the group consisting of Al, B, In, Ga, and mixtures of two or more thereof.

35. The zeolitic material of claim 25, wherein the zeolitic material comprises ZSM-5.

36. The zeolitic material of claim 25, wherein the BET surface area of the zeolitic material determined according to DIN 66131 ranges from 200 to 900 m²/g.

37. The zeolitic material of claim 25, wherein the zeolitic material displays a water uptake of 10.0 wt.-% or less.

38. A process for the conversion of oxygenates to olefins comprising (I) providing a gas stream comprising one or more oxygenates; (II) contacting the gas stream with a catalyst comprising a zeolitic material according to claim 25.

39. The process of claim 38, wherein the gas stream provided in step (I) contains one or more oxygenates selected from the group consisting of aliphatic alcohols, ethers, carbonyl compounds, and mixtures of two or more thereof.

40. The process of claim 38, wherein the gas stream provided in step (I) contains from 30 to 100 vol.-% of oxygenates based on the total volume of the gas stream.

41. The process of claim 38, wherein the gas stream provided in step (i) contains 60 vol.-% or less of water based on the total volume of the gas stream.

42. The process of claim 38, wherein contacting of the gas stream with the catalyst in step (II) is performed at a temperature in the range of 200 to 700° C.

43. The process of claim 38, wherein contacting of the gas stream with the catalyst in step (II) is performed at a pressure in the range of 0.1 to 10 bar.

44. The process of claim 38, wherein the process is at least in part performed in a continuous mode.

45. The process of claim 44, wherein the weight hourly space velocity (WHSV) of the gas stream in step (II) ranges from 0.5 to 50 h⁻¹.

46. A method of catalyzing a reaction, the method comprising adding the zeolitic material of claim 25 as a molecular sieve, catalyst, catalyst support, and/or as an adsorbent.

47. The method of claim 46, wherein the reaction comprises continuous conversion of methanol to olefins at a methanol conversion rate of at least 97% for at least 124 hours.

48. The method of claim 46, wherein the reaction comprises continuous conversion of methanol to olefins with a selectivity of at least 35.5% for propylene.

* * * * *